(12) United States Patent
Daks et al.

(10) Patent No.: US 12,329,584 B2
(45) Date of Patent: Jun. 17, 2025

(54) METHODS AND APPARATUSES FOR COLLECTION OF ULTRASOUND DATA

(71) Applicant: BFLY OPERATIONS, INC., Burlington, MA (US)

(72) Inventors: Alon Daks, Scarsdale, NY (US); Audrey Howell, Brooklyn, NY (US); Christophe Meyer, New York, NY (US); Robert Schneider, Killingworth, CT (US)

(73) Assignee: BFLY Operations, Inc, Burlington, MA (US)

( * ) Notice: Subject to any disclaimer, the term of this patent is extended or adjusted under 35 U.S.C. 154(b) by 287 days.

(21) Appl. No.: 17/862,132

(22) Filed: Jul. 11, 2022

(65) Prior Publication Data

US 2023/0012014 A1    Jan. 12, 2023

Related U.S. Application Data

(60) Provisional application No. 63/220,954, filed on Jul. 12, 2021.

(51) Int. Cl.
*A61B 8/00* (2006.01)

(52) U.S. Cl.
CPC ............ *A61B 8/5223* (2013.01); *A61B 8/463* (2013.01); *A61B 8/5207* (2013.01)

(58) Field of Classification Search
CPC ..... A61B 8/5223; A61B 8/463; A61B 8/5207; A61B 8/461; A61B 8/54; G01S 15/899; G01S 7/52085
USPC ........................................................ 382/128
See application file for complete search history.

(56) References Cited

U.S. PATENT DOCUMENTS

| | | | |
|---|---|---|---|
| 6,200,267 B1 | 3/2001 | Burke | |
| 6,360,027 B1 | 3/2002 | Hossack et al. | |
| 10,702,242 B2 | 7/2020 | de Jonge et al. | |
| 10,709,415 B2 | 7/2020 | Neben et al. | |
| 10,856,840 B2 | 12/2020 | Rothberg et al. | |
| 10,856,848 B2 | 12/2020 | Gafner et al. | |
| D915,424 S | 4/2021 | Elgena et al. | |
| 10,993,697 B2 | 5/2021 | Nouri et al. | |

(Continued)

FOREIGN PATENT DOCUMENTS

| WO | WO 2017/222964 A1 | 12/2017 |
|---|---|---|
| WO | WO 2017/222970 A1 | 12/2017 |

OTHER PUBLICATIONS

U.S. Appl. No. 17/871,875, filed Jul. 22, 2022, Silberman et al.

(Continued)

*Primary Examiner* — Juan A Torres
(74) *Attorney, Agent, or Firm* — Boston & Galway, LLC

(57) ABSTRACT

Technology for guiding a user to collect clinically usable ultrasound images is described. In some embodiments, an ultrasound device may automatically change the elevational steering angle of its ultrasound beam (e.g., using beamforming) in order to collect ultrasound data from different imaging planes within the subject. A processing device in operative communication with the ultrasound device may select one of the collected ultrasound images based on its quality (e.g., select the ultrasound image having the highest quality), and then continue to collect ultrasound images using the elevational steering angle at which the selected ultrasound image was collected.

14 Claims, 14 Drawing Sheets

(56) References Cited

U.S. PATENT DOCUMENTS

| | | | |
|---|---|---|---|
| 11,266,380 B2* | 3/2022 | Carolus | A61B 8/483 |
| 2004/0006266 A1 | 1/2004 | Ustuner et al. | |
| 2005/0228284 A1 | 10/2005 | Baumgartner et al. | |
| 2006/0116578 A1 | 6/2006 | Grunwald et al. | |
| 2010/0191114 A1 | 7/2010 | Hyun et al. | |
| 2011/0055447 A1 | 3/2011 | Costa | |
| 2011/0112401 A1 | 5/2011 | Watanaba | |
| 2013/0345563 A1* | 12/2013 | Stuebe | A61B 5/316 600/440 |
| 2015/0002538 A1* | 1/2015 | Sohn | A61B 8/5223 345/629 |
| 2015/0150503 A1* | 6/2015 | Pamnani | A61B 8/4483 600/438 |
| 2016/0012582 A1 | 1/2016 | Mauldin, Jr. et al. | |
| 2016/0058426 A1 | 3/2016 | Hedlund et al. | |
| 2016/0063695 A1 | 3/2016 | Lee | |
| 2016/0148373 A1 | 5/2016 | Robinson et al. | |
| 2016/0174902 A1 | 6/2016 | Georgescu et al. | |
| 2016/0242740 A1 | 8/2016 | Day | |
| 2017/0143312 A1 | 5/2017 | Hedlund et al. | |
| 2017/0303899 A1 | 10/2017 | Willsie | |
| 2017/0360397 A1 | 12/2017 | Rothberg et al. | |
| 2017/0360401 A1 | 12/2017 | Rothberg et al. | |
| 2017/0360403 A1 | 12/2017 | Rothberg et al. | |
| 2017/0360404 A1 | 12/2017 | Gafner et al. | |
| 2017/0360411 A1 | 12/2017 | Rothberg et al. | |
| 2017/0360412 A1 | 12/2017 | Rothberg et al. | |
| 2018/0344293 A1 | 12/2018 | Raju et al. | |
| 2019/0059851 A1* | 2/2019 | Rothberg | A61B 8/42 |
| 2019/0125298 A1 | 5/2019 | Abolmaesumi et al. | |
| 2019/0142388 A1 | 5/2019 | Gonyeau et al. | |
| 2019/0196600 A1 | 6/2019 | Rothberg et al. | |
| 2019/0282208 A1 | 9/2019 | Silberman et al. | |
| 2019/0307428 A1 | 10/2019 | Silberman et al. | |
| 2020/0037986 A1 | 2/2020 | Silberman et al. | |
| 2020/0037987 A1 | 2/2020 | Silberman et al. | |
| 2020/0037998 A1* | 2/2020 | Gafner | A61B 8/54 |
| 2020/0046314 A1 | 2/2020 | Neben et al. | |
| 2020/0046322 A1 | 2/2020 | Silberman | |
| 2020/0054307 A1 | 2/2020 | Silberman et al. | |
| 2020/0069291 A1* | 3/2020 | Zaslavsky | A61B 8/4245 |
| 2020/0129151 A1 | 4/2020 | Neben et al. | |
| 2020/0129156 A1 | 4/2020 | Elgena et al. | |
| 2020/0211174 A1 | 7/2020 | Rothberg et al. | |
| 2020/0214672 A1 | 7/2020 | de Jonge et al. | |
| 2020/0214674 A1 | 7/2020 | Gafner et al. | |
| 2020/0214679 A1 | 7/2020 | Silberman et al. | |
| 2020/0214682 A1* | 7/2020 | Zaslavsky | G06T 19/003 |
| 2020/0261054 A1 | 8/2020 | Silberman et al. | |
| 2020/0289094 A1 | 9/2020 | de Jonge et al. | |
| 2020/0320694 A1 | 10/2020 | Howell et al. | |
| 2021/0038189 A1 | 2/2021 | Liu et al. | |
| 2021/0038191 A1 | 2/2021 | Hageman et al. | |
| 2021/0096243 A1 | 4/2021 | Gafner et al. | |
| 2021/0153846 A1 | 5/2021 | Bellamkonda et al. | |
| 2021/0169455 A1 | 6/2021 | Annangi et al. | |
| 2021/0408716 A1 | 12/2021 | Schneider et al. | |
| 2022/0061816 A1* | 3/2022 | Lee | A61B 8/5207 |

OTHER PUBLICATIONS

EP19784974.8, Dec. 6, 2021, Extended European Search Report.
PCT/US2019/026528, Jul. 1, 2019, International Search Report and Written Opinion.
PCT/US2019/026528, Oct. 22, 2020, International Preliminary Report on Patentability.
Extended European Search Report for European Application No. 19784974.8, dated Dec. 6, 2021.
International Search Report and Written Opinion mailed Jul. 1, 2019 in connection with International Application No. PCT/US2019/026528.
International Preliminary Report on Patentability mailed Oct. 22, 2020 in connection with International Application No. PCT/US2019/026528.
Fienup et al., Aberration correction by maximizing generalized sharpness metrics. Journal of Optical Society of America A. 2003: 20(4): 609-620.
Kragh et al., Monotonic Iterative Algorithm for Minimum-Entropy Autofocus. Adaptive Sensor Array Processing (ASAP) Workshop. Jun. 2006; 6 pages.
Rudin et al., Nonlinear total variation based noise removal algorithms. Physica D: nonlinear phenomena. 1992: 60.1-4; 259-268.

* cited by examiner

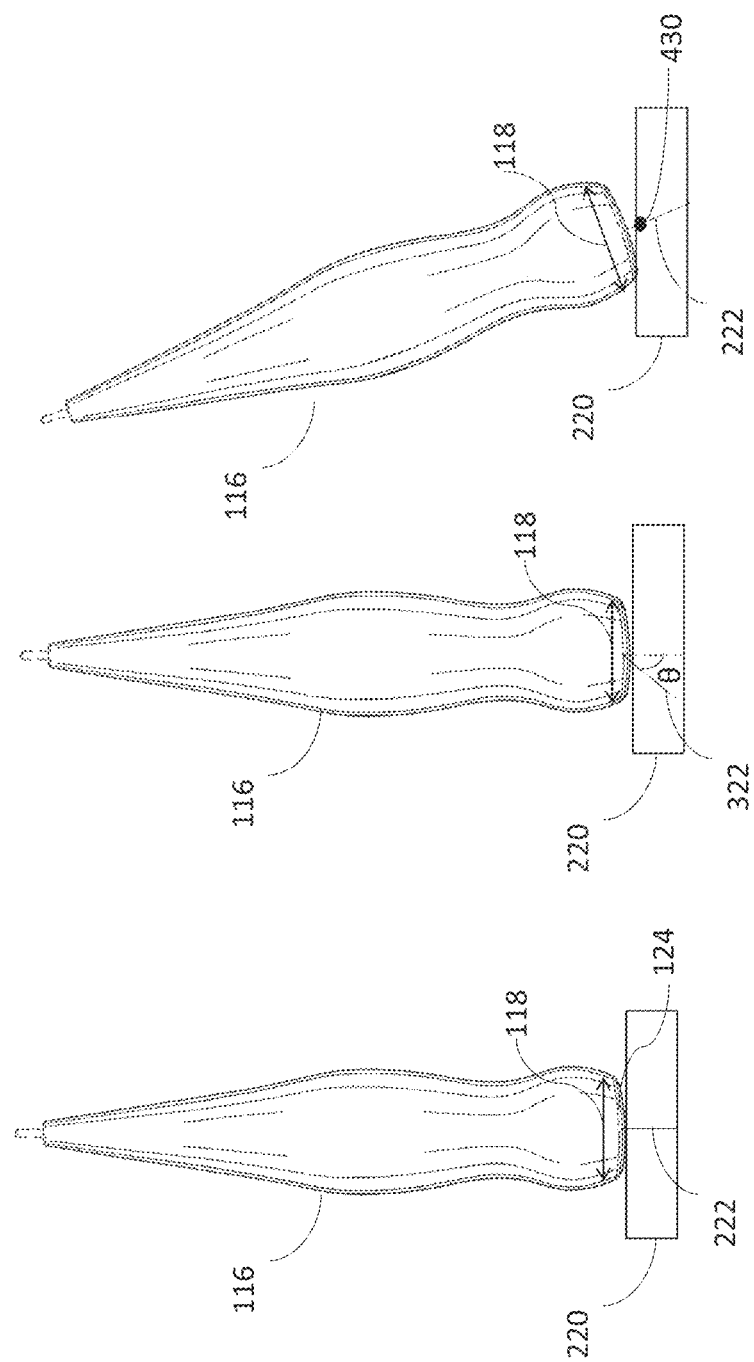

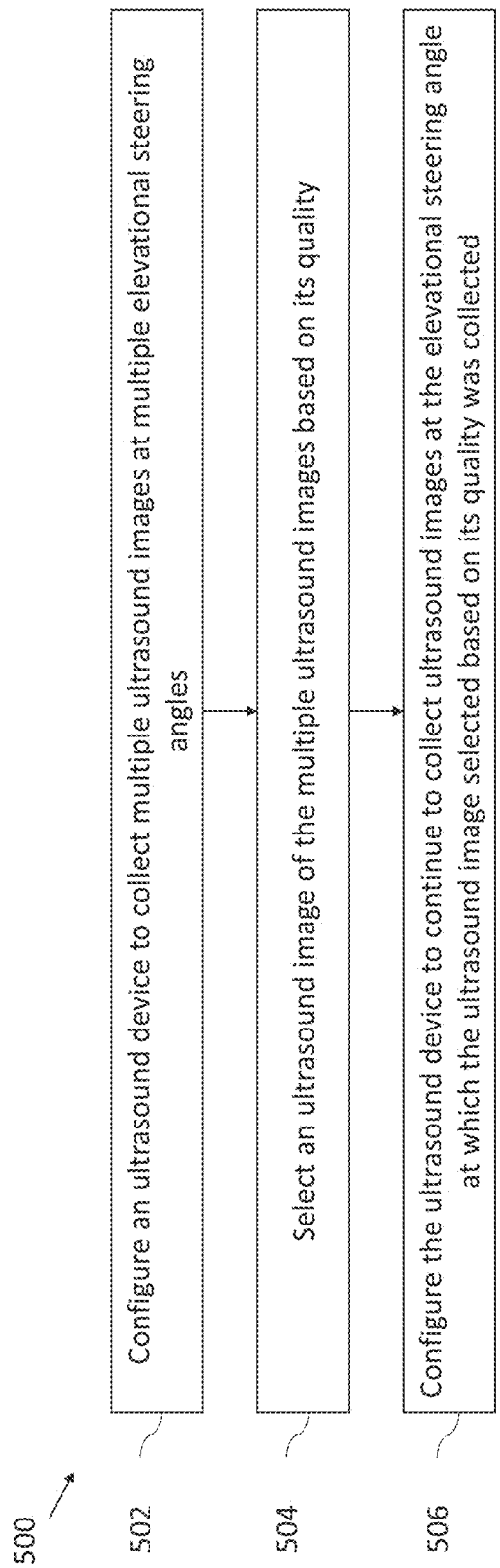

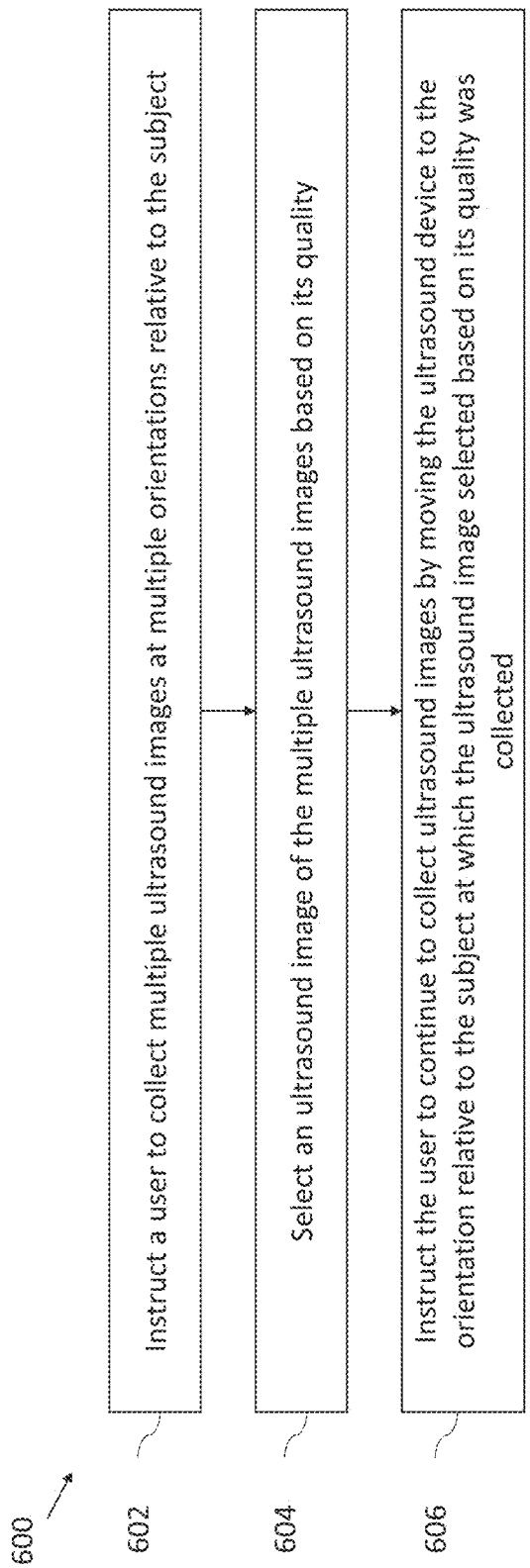

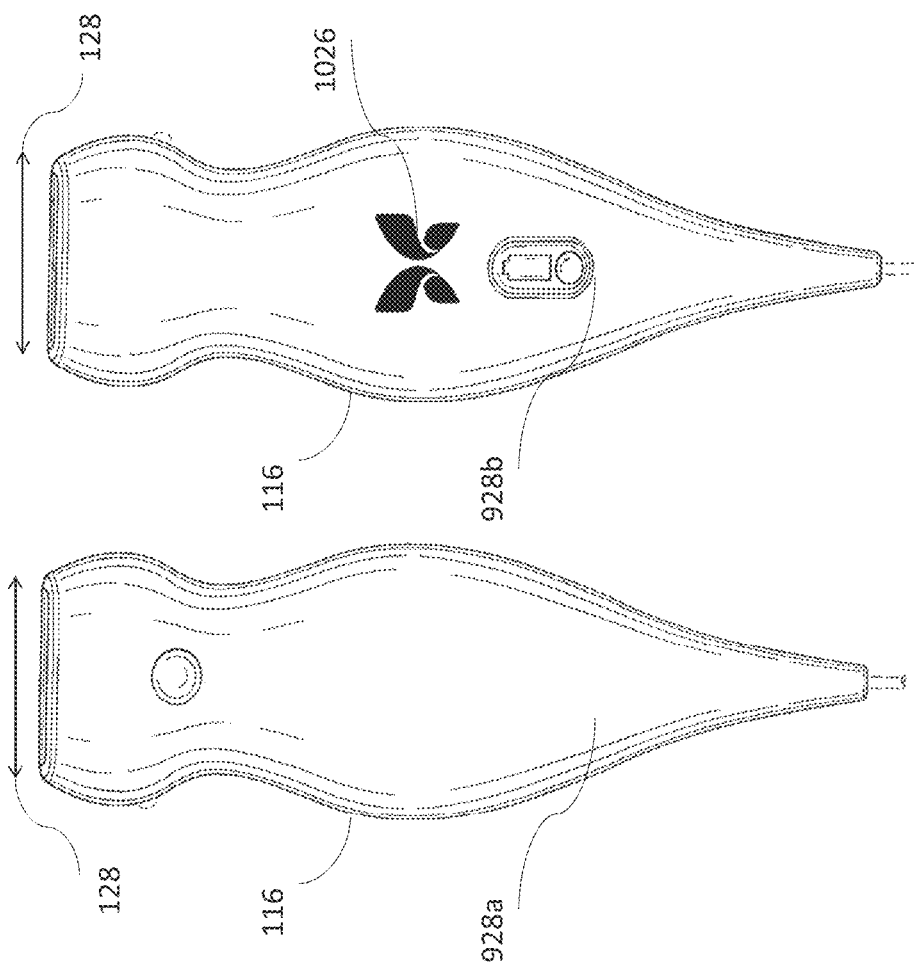

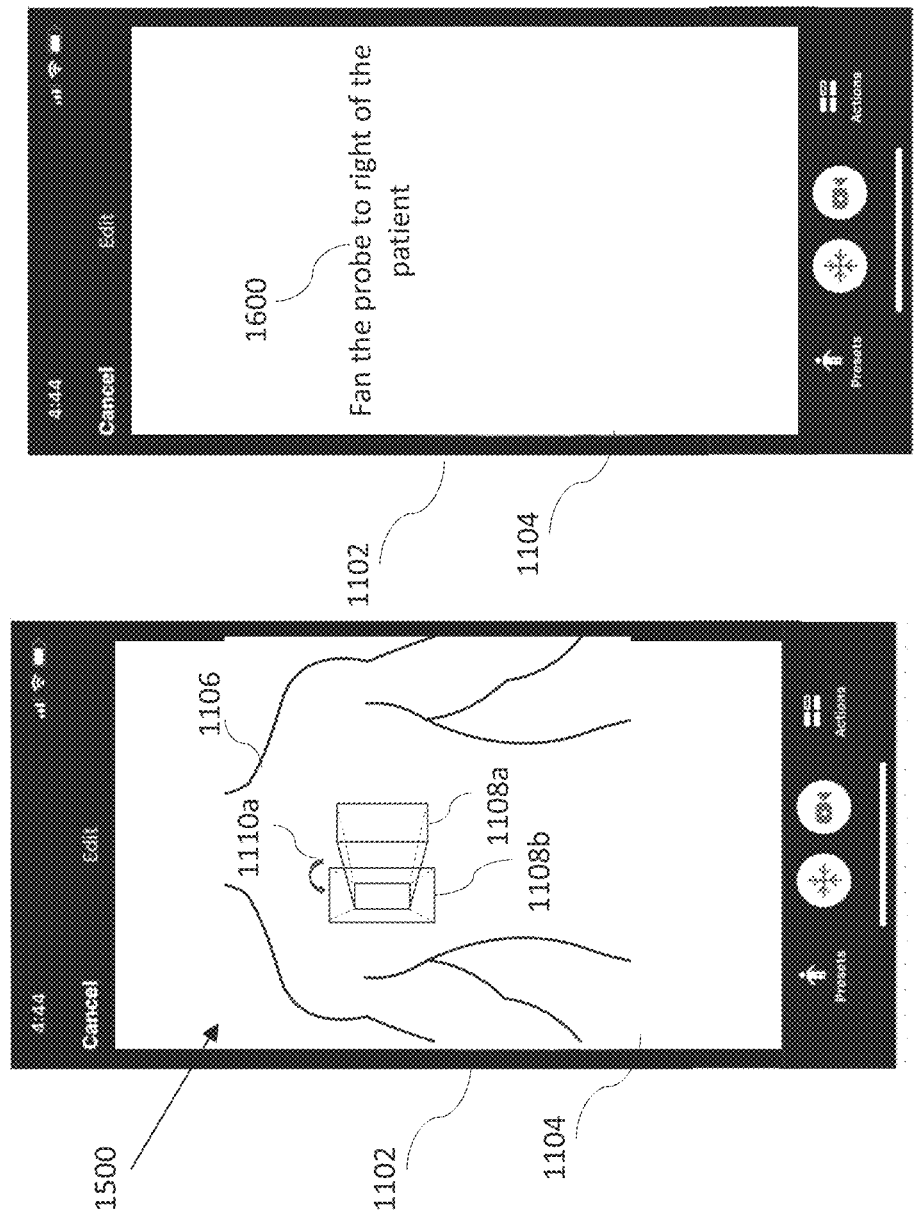

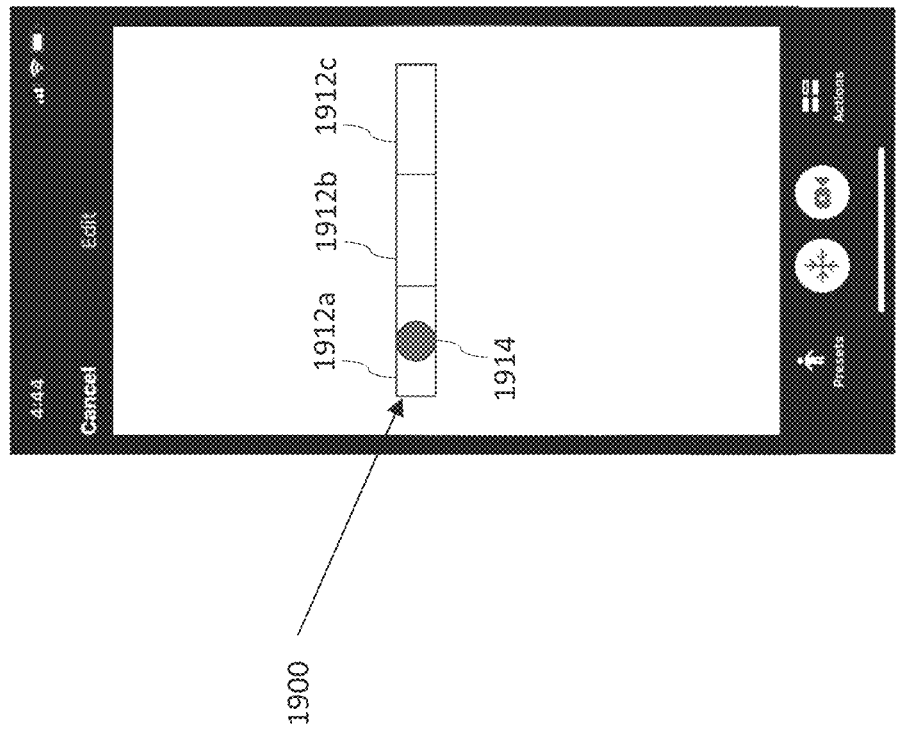

METHODS AND APPARATUSES FOR COLLECTION OF ULTRASOUND DATA

CROSS-REFERENCE TO RELATED APPLICATIONS

The present application claims the benefit under 35 U.S.C. § 119(e) of U.S. Provisional Patent Application Ser. No. 63/220,954, filed Jul. 12, 2021, and entitled "METHODS AND APPARATUSES FOR COLLECTION OF ULTRASOUND DATA," which is hereby incorporated by reference herein in its entirety.

FIELD

Generally, the aspects of the technology described herein relate to collection of ultrasound data, methods of operating ultrasound devices, and the ultrasound devices themselves.

BACKGROUND

Ultrasound devices may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, an apparatus is provided, comprising a processing device in operative communication with an ultrasound device. The processing device is configured to: instruct a user to collect multiple ultrasound images at multiple orientations relative to a subject; select an ultrasound image of the multiple ultrasound images based on its quality; and instruct the user to continue to collect ultrasound images by moving the ultrasound device to an orientation of the multiple orientations relative to the subject at which the ultrasound image selected based on its quality was collected.

According to one aspect, a method is provided, comprising: instructing, with a processing device in operative communication with an ultrasound device, a user to collect multiple ultrasound images at multiple orientations relative to a subject using the ultrasound device; selecting, with the processing device, an ultrasound image of the multiple ultrasound images based on its quality; and instructing, with the processing device, the user to continue to collect ultrasound images by moving the ultrasound device to an orientation of the multiple orientations relative to the subject at which the ultrasound image selected based on its quality was collected.

According to an aspect of the present disclosure, at least one non-transitory computer-readable storage medium is provided storing processor-executable instructions that, when executed by at least one processor on a processing device in operative communication with an ultrasound device, cause the processing device to: instruct a user of the ultrasound device to collect multiple ultrasound images at multiple orientations relative to a subject; select an ultrasound image of the multiple ultrasound images based on its quality; and instruct the user to continue to collect ultrasound images by moving the ultrasound device to an orientation of the multiple orientations relative to the subject at which the ultrasound image selected based on its quality was collected.

According to one aspect, an apparatus is provided, comprising a processing device in operative communication with an ultrasound device, the processing device configured to: configure the ultrasound device to collect multiple ultrasound images from a subject at multiple elevational steering angles; select an ultrasound image of the multiple ultrasound images based on its quality; and instruct a user to continue to collect ultrasound images by moving the ultrasound device to an orientation relative to the subject corresponding to an elevational steering angle at which the ultrasound image selected based on its quality was collected.

According to one aspect, a method is provided, comprising: configuring, with a processing device in operative communication with an ultrasound device, the ultrasound device to collect multiple ultrasound images from a subject at multiple elevational steering angles; selecting, with the processing device, an ultrasound image of the multiple ultrasound images based on its quality; and instructing, with the processing device, a user to continue to collect ultrasound images by moving the ultrasound device to an orientation relative to the subject corresponding to an elevational steering angle at which the ultrasound image selected based on its quality was collected.

According to one aspect, at least one non-transitory computer-readable storage medium is provided storing processor-executable instructions that, when executed by at least one processor on a processing device in operative communication with an ultrasound device, cause the processing device to: configure the ultrasound device to collect multiple ultrasound images from a subject at multiple elevational steering angles; select an ultrasound image of the multiple ultrasound images based on its quality; and instruct a user to continue to collect ultrasound images by moving the ultrasound device to an orientation relative to the subject corresponding to an elevational steering angle at which the ultrasound image selected based on its quality was collected.

According to one aspect, an apparatus is provided, comprising a processing device in operative communication with an ultrasound device, the processing configured to: instruct a user to collect multiple ultrasound images at multiple orientations relative to a subject; select an ultrasound image of the multiple ultrasound images based on its quality; and configure the ultrasound device to continue to collect ultrasound images at an elevational steering angle corresponding to the orientation relative to the subject at which the ultrasound image selected based on its quality was collected.

According to one aspect, a method is provided, comprising: instructing, with a processing device in operative communication with an ultrasound device, a user of the ultrasound device to collect multiple ultrasound images at multiple orientations relative to a subject; selecting, with the processing device, an ultrasound image of the multiple ultrasound images based on its quality; and configuring, with the processing device, the ultrasound device to continue to collect ultrasound images at an elevational steering angle corresponding to the orientation relative to the subject at which the ultrasound image selected based on its quality was collected.

According to one aspect, at least one non-transitory computer-readable storage medium is provided storing processor-executable instructions that, when executed by at least one processor on a processing device in operative communication with an ultrasound device, cause the processing device to: instruct a user to collect multiple ultrasound images at multiple orientations relative to a subject; select an ultrasound image of the multiple ultrasound images based on its quality; and configure the ultrasound device to continue to collect ultrasound images at an elevational steering angle corresponding to the orientation relative to the subject at which the ultrasound image selected based on its quality was collected.

According to one aspect, an apparatus is provided, comprising a processing device in operative communication with an ultrasound device, the processing device configured to: configure the ultrasound device to collect multiple ultrasound images from a subject at multiple elevational steering angles; select an ultrasound image of the multiple ultrasound images based on its quality; and (a) instruct a user to continue to collect ultrasound images by moving the ultrasound device to an orientation relative to the subject corresponding to an elevational steering angle at which the ultrasound image selected based on its quality was collected; or (b) configure the ultrasound device to continue to collect ultrasound images at an elevational steering angle corresponding to the orientation relative to the subject at which the ultrasound image selected based on its quality was collected.

According to one aspect, a method is provided, comprising: configuring, with a processing device in operative communication with an ultrasound device, the ultrasound device to collect multiple ultrasound images from a subject at multiple elevational steering angles; selecting, with the processing device, an ultrasound image of the multiple ultrasound images based on its quality; and (a) instructing, with the processing device, a user to continue to collect ultrasound images by moving the ultrasound device to an orientation relative to the subject corresponding to an elevational steering angle at which the ultrasound image selected based on its quality was collected; or (b) configure the ultrasound device to continue to collect ultrasound images at an elevational steering angle corresponding to the orientation relative to the subject at which the ultrasound image selected based on its quality was collected.

According to one aspect, at least one non-transitory computer-readable storage medium is provided storing processor-executable instructions that, when executed by at least one processor on a processing device in operative communication with an ultrasound device, cause the processing device to: configure the ultrasound device to collect multiple ultrasound images from a subject at multiple elevational steering angles; select an ultrasound image of the multiple ultrasound images based on its quality; and (a) instruct a user to continue to collect ultrasound images by moving the ultrasound device to an orientation relative to the subject corresponding to an elevational steering angle at which the ultrasound image selected based on its quality was collected; or (b) configure the ultrasound device to continue to collect ultrasound images at an elevational steering angle corresponding to the orientation relative to the subject at which the ultrasound image selected based on its quality was collected.

According to an aspect, an apparatus is provided, comprising: a processing device in operative communication with an ultrasound device. The processing device is configured to: configure the ultrasound device to collect multiple ultrasound images from a subject at multiple elevational steering angles using beamforming while the ultrasound device is maintained stationary, the multiple ultrasound images including between approximately 4-50 ultrasound images; and select an ultrasound image of the multiple ultrasound images based on its quality using a statistical model. Selecting comprises one or more of: determining the quality of the selected ultrasound image by calculating a prediction of a collective opinion of a group of individuals regarding the clinical usability of the selected ultrasound image; determining the quality of the selected ultrasound image by determining a presence or absence of one or more landmarks in the selected ultrasound image; or determining the quality of the selected ultrasound image by determining a quality of the one or more landmarks in the selected ultrasound image. The processing device is further configured to (a) instruct a user to continue to collect ultrasound images by moving the ultrasound device to an orientation relative to the subject corresponding to an elevational steering angle at which the ultrasound image selected based on its quality was collected; or (b) configure the ultrasound device to continue to collect ultrasound images at an elevational steering angle corresponding to the orientation relative to the subject at which the ultrasound image selected based on its quality was collected. The processing device is a smartphone, tablet, or laptop in some embodiments.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIG. 2 illustrates an example of the ultrasound device of FIG. 1 imaging a subject, in accordance with certain embodiments described herein.

FIG. 3 illustrates another example of the ultrasound device of FIG. 1 imaging the subject, in accordance with certain embodiments described herein.

FIG. 4 illustrates another example of the ultrasound device of FIG. 1 imaging the subject, in accordance with certain embodiments described herein.

FIGS. 5, 6, 7, and 8 illustrate respective processes for collection of ultrasound images, in accordance with certain embodiments described herein.

FIGS. 9 and 10 illustrate two side views of the ultrasound device of FIG. 1, one of the sides including a feature (namely, an icon), in accordance with certain embodiments described herein.

FIG. 15 illustrates an example GUI for instructing a user to move the ultrasound device to continue to collect ultrasound images along the imaging plane at which an ultrasound image selected based on its quality was collected, in accordance with certain embodiments described herein.

FIG. 16 illustrates an example instruction for instructing a user to move the ultrasound device to continue to collect ultrasound images along the imaging plane at which an ultrasound image selected based on its quality was collected, in accordance with certain embodiments described herein.

FIG. 19 illustrates an example GUI for instructing a user to continue to collect ultrasound images along the imaging plane at which an ultrasound image selected based on its quality was collected, in accordance with certain embodiments described herein.

DETAILED DESCRIPTION

Figure 1:
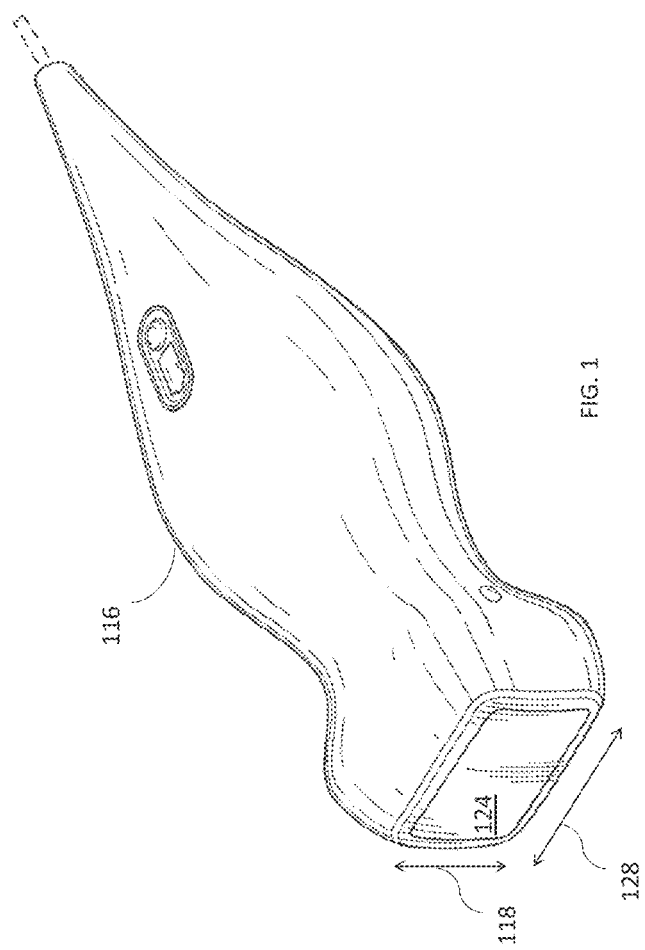
FIG. 1 illustrates an example ultrasound device, in accordance with certain embodiments described herein.
Figure 7:
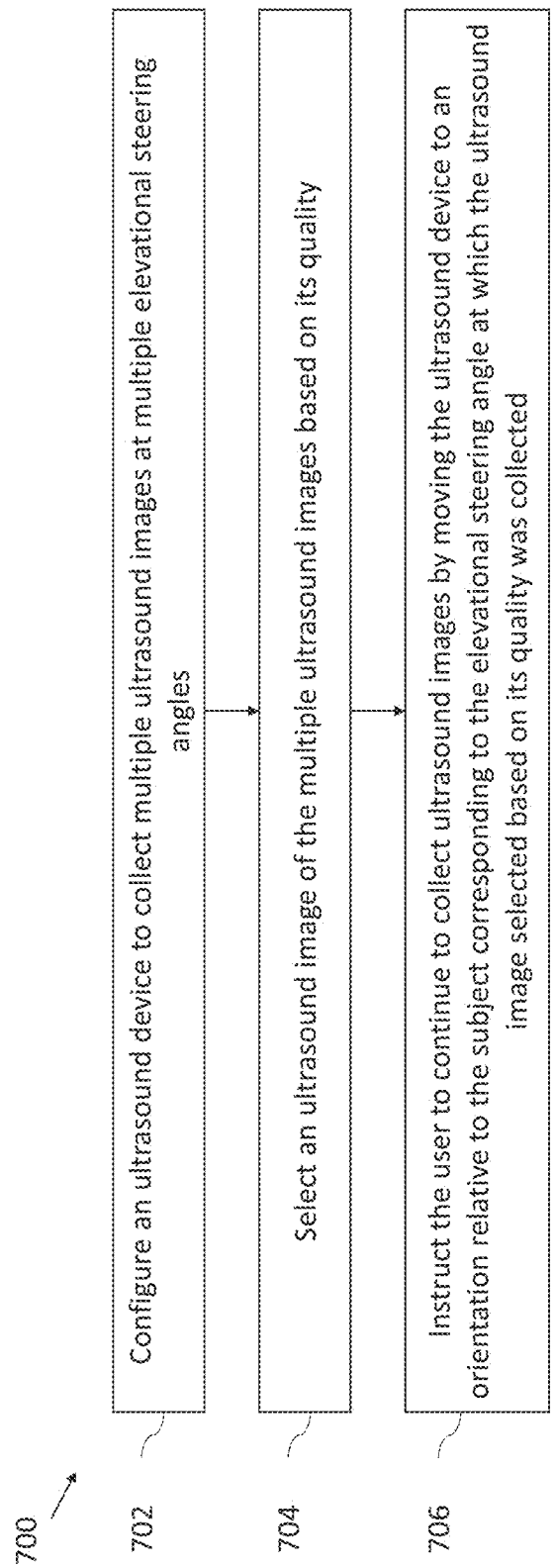
Figure 8:
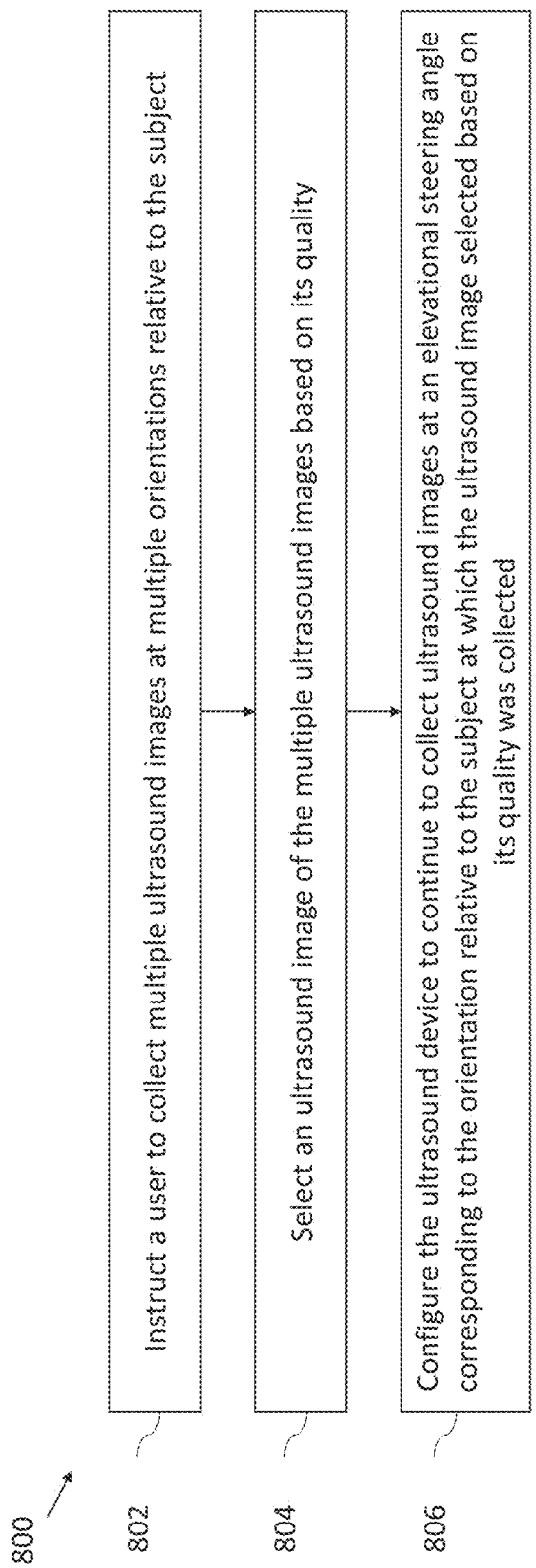

Conventional ultrasound systems are large, complex, and expensive systems that are typically only purchased by large medical facilities with significant financial resources. Recently, less expensive and less complex ultrasound imaging devices have been introduced. Such devices may include ultrasonic transducers monolithically integrated onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application), published as U.S. Pat. Pub. No. 2017/0360397 A1 and issued as U.S. Pat. No. 10,856,840 (the '840 patent), which is incorporated by reference herein in its entirety. The reduced cost and increased portability of these new ultrasound devices may make them significantly more accessible to the general public than conventional ultrasound devices.

The inventors have recognized and appreciated that although the reduced cost and increased portability of some ultrasound imaging devices, such as those described in the '840 patent, makes them more accessible to the general populace, people who could make use of such devices have little to no training for how to use them. Ultrasound examinations often include the acquisition of ultrasound images that contain a view of a particular anatomical structure (e.g., an organ) of a subject. Acquisition of these ultrasound images typically requires considerable skill. For example, when performing ultrasound imaging of the lungs, the orientation of the ultrasound device relative to the subject may be especially important for capturing a clinically usable ultrasound image of the lungs. In particular, acquiring a clinically usable ultrasound image of the lungs may require fanning the ultrasound device, which includes moving the ultrasound device in the short axis of the ultrasound device's ultrasound transducer array approximately about a fixed point on the subject while changing the angle of insonation relative to the subject away from 90 degrees. Fanning the ultrasound device may cause the ultrasound device to collect ultrasound images from different imaging planes within the subject, and the user may fan the ultrasound device until the correct imaging plane is found. Fanning may be a difficult maneuver for a novice user to perform, thus making it difficult for a novice user to capture a clinically usable ultrasound image of the lungs, or of any other anatomical region in which fanning may be helpful for capturing a clinically usable ultrasound image.

The inventors have developed technology for guiding a user to collect clinically usable ultrasound images. In some embodiments, an ultrasound device may automatically change the elevational steering angle of its ultrasound beam (e.g., using beamforming) in order to collect ultrasound data from different imaging planes within the subject. A processing device in operative communication with the ultrasound device may select one of the collected ultrasound images based on its quality (e.g., select the ultrasound image having the highest quality), and then continue to collect ultrasound images using the elevational steering angle at which the selected ultrasound image was collected.

The inventors have also recognized that certain ultrasound devices may not be able to automatically change the elevational steering angle of its ultrasound beam through a sufficiently large elevational steering angle range such that the ideal elevational steering angle will be reached. In other words, elevational steering angles beyond the ultrasound device's ability may produce higher quality ultrasound images than elevational steering angles within the ultrasound device's ability. The range of elevational steering angles through which an ultrasound device may be able to steer its ultrasound beam may be limited, at least in part, by its beamforming ability. Thus, the inventors have developed technology in which, in some embodiments, a processing device in operative communication with an ultrasound device may instruct a user to fan the ultrasound device to different orientations relative to the subject in order to collect ultrasound data from different imaging planes within the subject. The processing device may select one of the collected ultrasound images based on its quality (e.g., select the ultrasound image having the highest quality), and then guide the user to return the ultrasound device to the orientation at which the selected ultrasound image was collected and continue to collect ultrasound images at that orientation.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates an example ultrasound device 116, in accordance with certain embodiments described herein. The ultrasound device 116 includes an ultrasound transducer array 124. The ultrasound transducer array 124 has a short dimension 118, which may also be referred to as the elevational dimension, and a long axis dimension 128, which may also be referred to as the azimuthal dimension.

FIG. 2 illustrates an example of the ultrasound device 116 imaging a subject 220, in accordance with certain embodiments described herein. The ultrasound device 116 is oriented approximately orthogonal to the surface of the subject 220. The ultrasound device 116 generates an ultrasound beam 222, shown in simplified form as a single line in the side view of FIG. 2, which penetrates the subject 220. In the example of FIG. 2, the direction of the ultrasound beam 222 is 90 degrees relative to the short axis 118 of the ultrasound transducer array 124, which may also be referred to as an elevational steering angle of zero (0) degrees. Both the elevational steering angle and the orientation of the ultrasound device 116 relative to the subject 220 may determine, at least in part, the imaging plane within the subject 220 from which the ultrasound device 116 collects ultrasound data.

FIG. 3 illustrates another example of the ultrasound device 116 imaging the subject 220, in accordance with certain embodiments described herein. The ultrasound device 116 is at the same orientation relative to the subject 220 as in FIG. 2, namely oriented approximately orthogonal to the surface of the subject 220. The ultrasound device 116 generates an ultrasound beam 322, shown in simplified form as a single line in the side view of FIG. 3, which penetrates the subject 220 and is different from the ultrasound beam 222. In particular, in the example of FIG. 3, the elevational steering angle is not zero (0) degrees, but instead may assume a value (illustrated in FIG. 3 as θ) between zero degrees and 90 degrees, as a non-limiting example. As described above, both the elevational steering angle and the orientation of the ultrasound device 116 relative to the subject 220 may determine, at least in part, the imaging plane within the subject 220 from which the ultrasound device 116 collects ultrasound data. In the example of FIG. 3, the ultrasound device 116 collects ultrasound data from a different imaging plane than in FIG. 2 because the elevational steering angle of the ultrasound beam 322 is different than the elevational steering angle of the ultrasound beam 222.

It should be appreciated from the above that changing the elevational steering angle (e.g., from that of the ultrasound beam 222 to that of the ultrasound beam 322) may allow for collection of ultrasound data from different imaging planes within the subject 220. Changing the elevational steering angle may be referred to as elevational steering. An ultrasound device may perform elevational steering using beamforming. To implement beamforming, ultrasound circuitry in the ultrasound device 116 may apply different delays to transmitted and/or received ultrasound waves/data from different portions of the ultrasound transducer array 124 of the ultrasound device 116 (e.g., different delays for different elevational rows, where a row refers to a sequence of elements at the same position on the short axis 118 of the ultrasound transducer array). Additionally or alternatively, delays may be applied by a processing device (not illustrated) that receives ultrasound data received from the ultrasound device 116. This elevational steering may thus be performed automatically by the ultrasound device 116 and/ or a processing device, without requiring any movement of the ultrasound device 116 relative to the subject 220 by a user.

FIG. 4 illustrates another example of the ultrasound device 116 imaging the subject 220, in accordance with certain embodiments described herein. The ultrasound device 116 is at a different orientation relative to the subject 220 than in FIG. 2. In particular, the ultrasound device 116 has moved in the short axis 118 of the ultrasound device 116 approximately about a fixed point 430 on the subject 220 such that the ultrasound device 116 is not orthogonal to the surface of the subject 220. In the example of FIG. 4, the ultrasound device 116 generates the ultrasound beam 222, which has the same elevational steering angle (0 degrees) as in FIG. 2. As described above, both elevational steering angle and the orientation of the ultrasound device 116 relative to the subject 220 may determine, at least in part, the imaging plane within the subject 220 from which the ultrasound device 116 collects ultrasound data. In the example of FIG. 4, the ultrasound device collects ultrasound data from a different imaging plane than in FIG. 2 because the orientation of the ultrasound device 116 relative to the subject 220 in FIG. 4 is different than the orientation in FIG. 2.

A user may manually move the ultrasound device 116 from the orientation relative to the subject 220 in FIG. 2 to the orientation relative to the subject 220 in FIG. 4 in order to collect ultrasound data from different imaging planes. Moving the ultrasound device 116 in the short axis 118 of the ultrasound transducer array 124 approximately about a fixed point on the subject 220 and thereby changing the angle of insonation relative to the subject 220 away from 90 degrees (i.e., perpendicular to the subject 220) may be referred to as fanning the ultrasound device 116. Fanning may include changing the angle of insonation 5, 10, 15, 20, 25, 30, 35, 40, 45, 50, 55, 60, 65, 70, 75, 80, 85, 90, or any other suitable number of degrees away from perpendicular to the subject.

FIGS. 2-4 thus illustrate two methods for collecting ultrasound data from different imaging planes within the subject 220. One may be performed automatically by the ultrasound device 116 and/or a processing device in communication with the ultrasound device 116, and may include elevational beam steering. Another may be performed manually by the user and may include the user fanning the ultrasound device 116 relative to the subject 220.

FIGS. 5, 6, 7, and 8 illustrate processes 500, 600, 700, and 800, respectively, for collection of ultrasound images, in accordance with certain embodiments described herein. The processes 500, 600, 700, and 800 are performed by a processing device. The processing device may be, for example, a mobile phone, tablet, or laptop in operative communication with an ultrasound device (e.g., the ultrasound device 116). The processing device and the ultrasound device may communicate over a wired communication link (e.g., over Ethernet, a Universal Serial Bus (USB) cable or a Lightning cable) and/or over a wireless communication link (e.g., over a BLUETOOTH, WiFi, or ZIGBEE wireless communication link).

In act 502 of the process 500, the processing device configures an ultrasound device to collect multiple ultrasound images at multiple elevational steering angles (i.e., relative to the ultrasound transducer array of the ultrasound device). The multiple ultrasound images may be collected one after another. In some embodiments, the processing device may configure the ultrasound device to collect between or equal to approximately 4-50 (e.g., 4-12, 12-24, 24-48, or any other suitable number of) ultrasound images at different elevational steering angles. The different elevational steering angles may be in increments, for example, of 1, 2, 3, 4, 5, 6, 7, 8, 9, 10, or any other suitable number of degrees. Fanning may involve sweeping through a series of elevational steering angles (e.g., the angle θ shown in FIG. 3 above) in increments of any of the sizes described above. In some embodiments, fanning involves starting at a relatively large positive elevational steering angle (e.g., approximately 90 degrees) and sweeping through to a relatively large negative elevational steering angle (e.g., approximately −90 degrees) in increments of any of the sizes described above. In some embodiments, fanning involves starting at a small elevational steering angle, such as 0 degrees, and sweeping to a large positive or negative elevational steering angle. In some embodiments, fanning involves sweeping back and forth through elevational steering angles. In some embodiments, manual fanning may allow for a larger range of angles as part of a sweep than electronic control of the elevational steering angle, since some ultrasound imaging devices have a limitation to the degree of electronic elevational steering they can provide. When the elevational steering is controlled by the processing device, the processing device may configure the ultrasound device to collect each of the ultrasound images at a different elevational steering angle using beamforming. To implement beamforming, the processing device may control ultrasound circuitry in the ultrasound device to apply different delays to transmitted and/or received ultrasound signals from different portions of the ultrasound transducer array of the ultrasound device (e.g., different delays for different elevational rows, where a row refers to a sequence of elements at the same position on the short axis of the ultrasound transducer array). Additionally or alternatively, delays may be applied by the processing device when processing data received from the ultrasound device. Due to the ultrasound images being collected at different elevational steering angles, the ultrasound images may be collected along different imaging planes relative to the subject. In some embodiments, the ultrasound device may remain stationary while collecting the multiple ultrasound images. Example illustrations of an ultrasound device collecting ultrasound data at different elevational steering angles may be found with references to FIGS. 2 and 3. In some embodiments, the processing device may provide an instruction to the user to maintain the ultrasound device stationary while the ultrasound device collects the multiple ultrasound images during act 502. In some embodiments, the processing device may store each of the multiple ultrasound images (e.g., in memory on the processing device) along with an indication of the elevational steering angle used for collecting it.

In act 504, the processing device selects an ultrasound image of the multiple ultrasound images (collected in act 502) based on its quality. The processing device may determine a quality of some or all of the multiple ultrasound images and then, based on the respective quality of the ultrasound images, select one of the ultrasound images. In some embodiments, the processing device may select the ultrasound image having the highest quality among the collected ultrasound images. In some embodiments, the processing device may determine a group of ultrasound images having the highest qualities among all the collected ultrasound images, and select one ultrasound image from this group. As will be described below, in some embodiments, the processing device may use a statistical model to calculate the quality of the multiple ultrasound images.

In some embodiments, when determining the quality of an ultrasound image, the processing device may calculate a prediction of a collective opinion of a group of individuals regarding the clinical usability of the ultrasound image. In such embodiments, the prediction may be a prediction of the fraction of a group of individuals who would classify the ultrasound image as clinically usable. For example, if the ultrasound image is of the lungs, the prediction may be a prediction of the fraction of a group of medical professionals skilled in interpreting ultrasound images who would classify the ultrasound images as clinically usable for evaluating the lung surface for the presence of B-lines. A higher fraction may correspond to a higher quality. In some embodiments, to automatically calculate the prediction of the fraction of a group of individuals who would classify an ultrasound image as clinically usable, the processing device may use a statistical model. The statistical model may be stored on the processing device, or may be stored on another device (e.g., a server) and the processing device may access the statistical model on that other device. The statistical model may be trained on multiple ultrasound images, each set of training imaging data labeled with the fraction of the group of individuals who would classify the imaging data as clinically usable. For example, if each set of training imaging data includes an ultrasound image of the lungs, each set may be labeled with the fraction of a group of medical professionals skilled in interpreting ultrasound images who would classify the ultrasound images as clinically usable for evaluating the lung surface for the presence of B-lines. To collect this training data, each set of ultrasound images may be shown to multiple medical professionals, each medical professional may classify certain of the ultrasound images as clinically usable for evaluating the lung surface for the presence of B-lines, and the fraction of the medical professionals who classified each set of ultrasound images as clinically usable for evaluating the lung surface for the presence of B-lines may be calculated. Based on the training, the statistical model may learn to calculate a prediction of the fraction of the group of medical professionals skilled in interpreting ultrasound images who would classify a new ultrasound image of the lungs as clinically usable for evaluating the lung surface for the presence of B-lines.

In some embodiments, when determining the quality of an ultrasound image, the processing device may determine the presence or absence of landmarks in the ultrasound image. Landmarks may be any type of anatomical feature, such as an anatomical region or structure, that when present in an ultrasound image, may be viewed as an indication that the ultrasound image is clinically usable. Pleural lines, ribs, lungs, heart, and liver are examples of anatomical structures that may be identified in some embodiments. For example, an ultrasound image of the lungs may be deemed clinically usable for certain purposes when the ultrasound image includes two ribs, the pleural line, and A lines. As another example, an ultrasound image of Morison's pouch may be deemed clinically usable when the ultrasound image includes the liver and kidney. In some embodiment, more landmarks being present in an ultrasound image corresponds to a higher quality and fewer landmarks being present in an ultrasound image corresponds to a lower quality. In some embodiments, the processing device may use a statistical model to determine the presence or absence of landmarks. In such embodiments, the processing device may use a statistical model trained to determine the locations of particular landmarks as depicted in ultrasound images. The statistical model may be stored on the processing device or stored on another electronic device (e.g., a server) and accessed by the processing device. In some embodiments, the statistical model may be trained on multiple pairs of input and output training data sets as a segmentation model. Each set of input training data may be an ultrasound image depicting one or more landmarks. Each set of output training data may include multiple segmentation masks for each of the landmarks. Each segmented mask may include an array of values equal in size to the input training data ultrasound image, and pixels corresponding to locations within one of the landmarks in the ultrasound image are manually set to 1 and other pixels are set to 0. Based on this training data, the statistical model may learn to output, based on an inputted ultrasound image, one or more segmentation masks, where each pixel in a given mask has a value representing the probability that the pixel corresponds to a location within a landmark in the ultrasound image (values closer to 1) or outside the landmark (values closer to 0). The processing device may select all pixels in a given segmentation mask that have a value greater than a threshold value (e.g., 0.5) as being within a landmark. The processing device may do this for all the segmentation masks in order to determine the locations of multiple landmarks in the ultrasound image. In some embodiments, the processing device may determine the presence or absence of landmarks based on segmentation masks. In some embodiments, the processing device may analyze a segmentation mask to determine if the corresponding landmark is present in the ultrasound image using various heuristics. For example, using heuristics may include determining whether the number of pixels determined to be within the landmark in the segmentation mask ("segmented pixels") is greater than a threshold number and/or analyzing various other relationships between the segmented pixels, such as how continuous they are (e.g., using connected components analysis).

In some embodiments, when determining the quality of an ultrasound image, the processing device may determine a quality of one or more landmarks in the ultrasound image (where the landmarks may be identified as described above). For example, in an ultrasound image of the lungs, the quality may be related to the height of the pleural line in the ultrasound image (where the pleural line may be a landmark). The processing device may measure the height of the pleural line in multiple ultrasound images and determine the quality of the ultrasound image to be proportional to the pleural line height. Thus, in embodiments in which ultrasound images of the lungs are collected and the processing device selects the ultrasound image having the highest quality, the image(s) identified as having the highest quality may be identified as such based on the pleural line in that image being of maximal height. In some embodiments, to measure the height of the pleural line in an ultrasound image, the processing device may determine the vertical position of the top of a segmented portion of the ultrasound image corresponding to the pleural line.

In some embodiments, when determining the quality of an ultrasound image, the processing device may identify a pathology or other imaging features of interest. For example, B-lines may be identified. The identification of pathology or other imaging features may be performed automatically in some embodiments. In some embodiments, identification is performed automatically using a statistical model or a machine learning model. Techniques for identifying features in images that may be used in embodiments of the present application are described in U.S. application Ser. No. 17/586,508 filed Jan. 27, 2022 and entitled "METHODS AND APPARATUSES FOR PROVIDING INDICATIONS OF MISSING LANDMARKS IN ULTRASOUND IMAGES," which is incorporated by reference herein in its entirety.

In some embodiments, the determination of quality of an image or series of images is based on just one of the clinical usability of the image, the presence of an anatomical feature or landmark, or the quality of a landmark.

In some embodiments, the processing device may use a combination of a prediction of a collective opinion of a group of individuals regarding the usability of the ultrasound image, a determination of the presence or absence of landmarks in the ultrasound image to determine the quality of the ultrasound device, and a quality of one or more landmarks in the ultrasound image. Such combination may include any one or more of the listed factors. Some such embodiments are now described.

In some embodiments, the ultrasound image with the highest score for clinical usability together with whether either B-lines or A-lines are present is selected as the highest quality image. If no anatomy is present in the image, then the image for which the quality is highest based on clinical usability of the image is selected. In some embodiments, instead of clinical usability, a different measure of quality is used in combination with whether an anatomical feature of interest is present in the image.

In some embodiments, the ultrasound image for which two ribs are identified is selected as the highest quality image even if other aspects of the quality of the image such as the clinical usability are higher for a view with only a single rib.

In some embodiments, the ultrasound image selected as the one with the highest quality is the image with the most B-lines, or the most segmented A-lines pixels, or the highest quality as measured by some other metric such as clinical usability. In some embodiments, B-lines and A-lines are counted in a different manner. The B-lines, which may be considered radial artifacts, are counted in 1-D radial space in some embodiments. The A-lines are counted in 2-D pixel space in some embodiments.

In some embodiments, various weighting schemes may be applied to different measures of quality of an image. In some embodiments, the clinical usability of an ultrasound image, the presence of a feature of interest in the image, and the quality of a feature of interest in the image may be assigned weights. The overall quality of the image may be determined as a weighted combination of those factors. The weights may be static or dynamic, varying over time. In some embodiments, heuristics are used to combine the various factors impacting quality.

Thus, it should be appreciated that the quality used in act 504, and similar acts in subsequent figures described herein, may be based on a variety of factors, individually or in combination.

In act 506, the processing device configures the ultrasound device to continue to collect ultrasound images at the elevational steering angle at which the ultrasound image selected based on its quality (in act 504) was collected. As described above, each of the multiple ultrasound images may have been stored (e.g., in memory on the processing device) along with an indication of the elevational steering angle used for collecting it. Thus, the processing device may determine the elevational steering angle at which the ultrasound image selected based on its quality was collected based on the indication stored along with this ultrasound image. The processing device may then configure the ultrasound device to collect further ultrasound images at this elevational steering angle (e.g., using beamforming as described with reference to act 502). In some embodiments, the ultrasound device may remain stationary during collection of the ultrasound images in act 502, the determination in act 504, and collection of the ultrasound image in act 506. In some embodiments, the processing device may provide an instruction to the user to maintain the ultrasound device stationary during acts 502, 504, and 506.

In act 602 of the process 600, the processing device instructs a user to collect multiple ultrasound images at different orientations relative to the subject. The instruction may be for the user to manually fan the ultrasound device on the subject. As described above, fanning an ultrasound device may include moving the ultrasound device in the short axis of the ultrasound device's transducer array approximately about a fixed point on the subject while changing the angle of insonation relative to the subject away from 90 degrees. Example illustrations of an ultrasound device collecting ultrasound data at different orientations relative to the subject through fanning may be found with references to FIGS. 2 and 4. The processing device may display the instruction on a display screen of the processing device and/or may output it as audio from a speaker of the processing device. In some embodiments, the processing device may configure the ultrasound device to use a constant elevational steering angle (e.g., zero degrees) relative to the ultrasound transducer array during collection of the ultrasound images in act 602. Further description of example instructions to the user may be found with reference to FIG. 11-14. As will be described below, in some embodiments the instructions may include a graphical user interface including an image of a subject and images of an ultrasound device in different orientations relative to the image of the subject. In some embodiments, the instructions may include a graphical user interface including images of an ultrasound device in different orientations, as well as an icon or other feature on the ultrasound device. In some embodiments, the instructions may include text.

As the user fans the ultrasound device, the ultrasound device may collect ultrasound images (e.g., at a rate of at least 5 Hz, at least 10 Hz, at least 20 Hz, at a rate between 5 and 60 Hz, and/or at a rate of more than 20 Hz). Due to the fanning of the ultrasound device, each of the ultrasound images may be collected along a different imaging plane relative to the subject. The ultrasound device may include one or more orientation sensors, such as an accelerometer, gyroscope, and/or magnetometer, and the processing device may collect data regarding the orientation of the ultrasound device from the one or more of the ultrasound device's orientation sensors when each ultrasound image is collected. Each orientation may correspond to a particular imaging plane. For example, if the subject is standing and the ultrasound device is oriented orthogonal to the direction of gravity, this orientation may correspond to an imaging plane closer to ninety degrees relative to the subject than if the ultrasound device is oriented at an acute angle relative to the direction of gravity. In some embodiments, the processing device may store each of the multiple ultrasound images (e.g., in memory on the processing device) along with an indication of the orientation (as collected by the orientation sensors) used for collecting it.

In act 604, the processing device selects an ultrasound image of the multiple ultrasound images (collected in act 602) based on its quality. This may be done in the manner described with reference to act 504, or in any other suitable manner.

In act 606, the processing device instructs the user to continue to collect ultrasound images by moving the ultrasound device to the orientation relative to the subject at which the ultrasound image selected based on its quality (in act 604) was collected. As described above, each of the multiple ultrasound images may have been stored (e.g., in memory on the processing device) along with an indication of the orientation (as collected by the orientation sensors) used for collecting it. Thus, the processing device may determine the orientation, which may correspond to a particular imaging plane, at which the ultrasound image selected based on its quality was collected, based on the indication stored along with this ultrasound image. The processing device may then instruct the user to fan the ultrasound device such that the ultrasound device may collect further ultrasound images at this orientation and along this imaging plane. For example, the processing device may monitor the current orientation of the ultrasound device (as determined by the orientation sensors) and provide instructions for fanning the ultrasound device such that its orientation becomes nearer to the orientation at which the ultrasound image selected based on its quality was collected. As a specific example, the orientation at which the ultrasound image selected based on its quality was collected may be the orientation when the ultrasound device is perpendicular to the surface of the subject. However, based on the orientation sensors, the processing device may determine that the ultrasound device is angled towards one direction of the subject, such as to the left of the subject. Thus, the processing device may provide an instruction to fan the ultrasound device such that it is angled more perpendicular to the surface of the subject. Once the ultrasound device is at the correct orientation, the processing device may cease to provide instructions for fanning the ultrasound device or provide an instruction to stop fanning the ultrasound device. The processing device may display the instruction on a display screen of the processing device and/or may output it as audio from a speaker of the processing device. Further description of example instructions to the user for moving the ultrasound device may be found with reference to FIGS. 15-19. As will be described below, in some embodiments the instructions for moving the ultrasound device may include a graphical user interface including an image of a subject and multiple images of an ultrasound device in different orientations relative to the image of the subject. In some embodiments, the instructions may include a graphical user interface including images of an ultrasound device in different orientations, as well as an icon or other feature on the ultrasound device. In some embodiments, the instructions may include text. In some embodiments, the instructions may include a graphical user interface including a left section, a center section, a right section, and a marker having a position within the left section, the center section, and/or the right section corresponding to a current orientation of the ultrasound device relative to the subject. In some embodiments, the graphical user interface may operate in the manner of a bubble level. Further description of example instructions to the user to stop moving the ultrasound device once it is at the correct orientation may be found with reference to FIGS. 20-21.

In act 702 of the process 700, the processing device configures an ultrasound device to collect multiple ultrasound images at multiple elevational steering angles (i.e., relative to the ultrasound transducer array of the ultrasound device). Act 702 may be performed in the same manner as act 502 or in any other suitable manner.

In act 704, the processing device selects an ultrasound image of the multiple ultrasound images (collected in act 702) based on its quality. Act 704 may be performed in the same manner as act 504, or in any other suitable manner.

In act 706, the processing device instructs the user to continue to collect ultrasound images by moving the ultrasound device to an orientation relative to the subject corresponding to the elevational steering angle at which the ultrasound image selected based on its quality was collected. As described above, each of the multiple ultrasound images may have been stored (e.g., in memory on the processing device) along with an indication of the elevational steering angle used for collecting it. Thus, the processing device may determine the elevational steering angle at which the ultrasound image selected based on its quality was collected based on the indication stored along with this ultrasound image. The processing device may then instruct the user to fan the ultrasound device such that the ultrasound device may collect further ultrasound images at an orientation relative to the subject corresponding to the elevational steering angle at which the ultrasound image selected based on its quality was collected. As a specific example, the elevational steering angle at which the ultrasound image selected based on its quality was collected may be 20 degrees (relative to the subject, assuming the ultrasound device was perpendicular). The processing device may thus instruct the user to fan the ultrasound device until it is tilted 20 degrees relative to the subject, and collect further ultrasound images using an elevational steering angle of 0 degrees. If, for example, the processing device determines, based on the orientation sensors, that the ultrasound device is perpendicular relative to the subject, then the processing device may provide an instruction to fan the ultrasound device such that it is angled more relative to the subject. The processing device may monitor the current orientation of the ultrasound device (as determined by the orientation sensors) and once the ultrasound device is at the correct orientation, the processing device may cease to provide instructions for fanning the ultrasound device or provide an instruction to stop fanning the ultrasound device. Further description of such instructions may be found with reference to act 606 and FIGS. 15-21.

In act 802 of the process 800, the processing device instructs a user to collect multiple ultrasound images at different orientations relative to the subject. Act 802 may be performed in the same manner as act 602, or in any other suitable manner.

In act 804, the processing device selects an ultrasound image of the multiple ultrasound images (collected in act 802) based on its quality. Act 804 may be performed in the same manner as act 504, or in any other suitable manner.

In act 806, the processing device configures the ultrasound device to continue to collect ultrasound images at an elevational steering angle corresponding to the orientation relative to the subject at which the ultrasound image selected based on its quality was collected. As described above, each of the multiple ultrasound images may have been stored (e.g., in memory on the processing device) along with an indication of the orientation (as collected by the orientation sensors) used for collecting it. Thus, the processing device may determine the orientation, which may correspond to a particular imaging plane, at which the ultrasound image selected based on its quality was collected, based on the indication stored along with this ultrasound image. The processing device may then configure the ultrasound device to collect further ultrasound images at this elevational steering angle (e.g., using beamforming as described with reference to act 502). As a specific example, the ultrasound device may have been tilted 20 degrees relative to the subject when the ultrasound image selected based on its quality was collected. The processing device may then configure the ultrasound device to use an elevational steering angle of 20 degrees in act 806. In some embodiments, the ultrasound device may remain stationary during collection of the ultrasound images in act 806. In some embodiments, the processing device may provide an instruction to the user to maintain the ultrasound device stationary during act 806.

The processes 500, 600, 700, and 800 may be used individually or in combination. In some embodiments, the process 700 is followed by the process 500. In some embodiments, the process 500 is followed by the process 700.

In some embodiments, a process of collecting ultrasound images comprises automatically configuring the ultrasound device to collect multiple ultrasound images at multiple elevational steering angles, followed by selecting an ultrasound image as the best based on its quality, using any of the manners described herein for determining image quality. If the image identified as best is, for example, the last image in the sweep and/or not determined to be of sufficiently high quality, the process proceeds by instructing the user to fan the ultrasound device, followed by automatically configuring the ultrasound device to collect multiple ultrasound images from another set of elevational steering angles. This subsequent set of steering angles may be considered multiple second elevational steering angles. An ultrasound image may then be selected from the subsequent set of ultrasound images based on its quality. Subsequently, the ultrasound device may be automatically configured to continue collecting ultrasound images at the elevation steering angle of the multiple second elevational steering angles determined to produce the best quality ultrasound image.

Operation in the manner just described may provide benefits in various situations. In some embodiments, the initial automatic collection of multiple ultrasound images at multiple elevational steering angles may result in selection of an ultrasound image of insufficient quality. By instructing the user to then fan the ultrasound device, the chance of the user positioning the ultrasound device within an acceptable angle in which automatic operation can proceed successfully may be increased. The system may then resume automatic operation as described. That is, the automatic collection of ultrasound images from multiple elevational steering angles may, in some embodiments, have a limited ability to compensate for imprecise angling of the ultrasound device by the user. Having the user fan the ultrasound device may result in the ultrasound device being angled within a window in which automatic control of elevational steering angles may then proceed successfully to collect multiple ultrasound images from multiple elevational steering angles to identify an ultrasound image of sufficient quality.

In some embodiments, when a processing device provides instructions to a user for moving an ultrasound device (e.g., as part of acts 602, 606, 706, and/or 802), the processing device may provide instructions relative to the subject. Example instructions provided relative to the subject may be found below with reference to FIGS. 11, 12, 15, and 16. In some embodiments, when a processing device provides instructions to a user for moving an ultrasound device, the processing device may provide instructions relative to a feature of the ultrasound device (e.g., relative to an icon on one side of the ultrasound device, as described with reference to FIGS. 9 and 10). Example instructions provided relative to a feature of the ultrasound device may be found below with reference to FIGS. 13, 14, 17, and 18. In some embodiments, prior to providing instruction to a user for moving the ultrasound device (e.g., as part of acts 602, 606, 706, and/or 802), the processing device may provide instructions to the user for orienting the ultrasound device in a default orientation relative to the subject. For example, the default orientation may be one in which a feature of the ultrasound device faces a particular direction relative to the subject.

FIGS. 9 and 10 illustrates two side views of the ultrasound device 116, one of the sides including a feature (namely, an icon), in accordance with certain embodiments described herein. In particular, FIG. 9 illustrates one side 928a of the ultrasound device 116 along the long dimension 128 of the ultrasound device. FIG. 10 illustrates the opposite side 928b of the ultrasound device 116 along the long dimension 128 of the ultrasound device 116. The side 928b of the ultrasound device has an icon 1026 while the side 928a of the ultrasound device does not have an icon.

Figure 11:
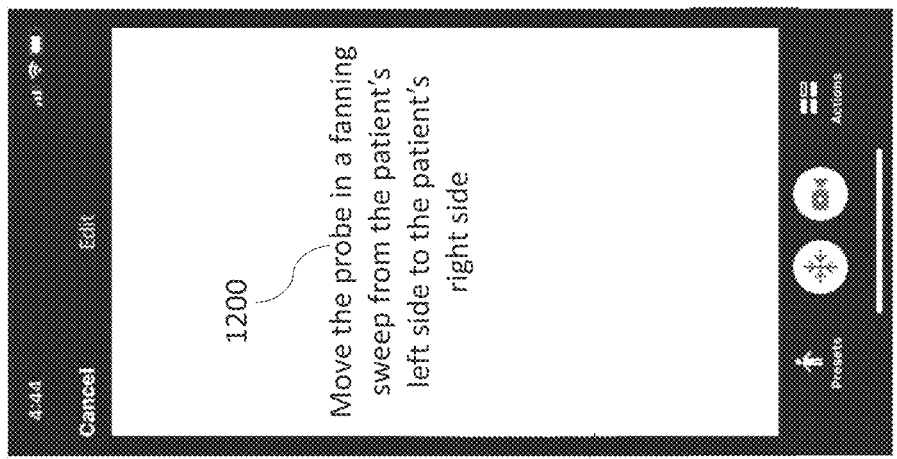
FIG. 11 illustrates an example graphical user interface (GUI) for instructing a user to collect multiple ultrasound images at multiple elevational steering angles, in accordance with certain embodiments described herein.

FIG. 11 illustrates an example graphical user interface (GUI) 1100 for instructing a user to collect multiple ultrasound images at multiple elevational steering angles, in accordance with certain embodiments described herein. The GUI 1100 is displayed on a display screen 1104 of a processing device 1102 (e.g., the processing device described with reference to the process 600). The GUI 1100 may be displayed in conjunction with acts 602 and/or 802. The GUI 1100 includes an image of a subject 1106; three images of an ultrasound device in different orientations (i.e., relative to the subject) 1108a, 1108b, and 1108c; and arrows 1110a and 1110b. The arrow 1110a points from the image of the ultrasound device in the orientations 1108a to the image of the ultrasound device in the orientation 1108b. The arrow 1110b points from the image of the ultrasound device in the orientation 1108b to the image of the ultrasound device in the orientation 1108c. Each of the images of the ultrasound device in the different orientations 1108a, 1108b, and 1108c may illustrate the ultrasound device at three different orientations during fanning. In other words, each of the images of the ultrasound device in the different orientations 1108a, 1108b, and 1108c may illustrate the ultrasound device at different angles of insonation when moving the ultrasound device in the short axis of the ultrasound device's transducer array approximately about a fixed point on the subject 1106. In still other words, the images of the ultrasound device in the different orientations 1108a, 1108b, and 1108c may illustrate the ultrasound device when collecting ultrasound images along different imaging planes relative to the subject 1106. In particular, the image of the ultrasound device at the orientation 1108a illustrates an orientation in which the ultrasound device is angled from the surface of the subject 1106 to the left of the subject 1106 (i.e., left from the perspective of the subject 1106). Thus, if the elevational steering angle from the ultrasound device is zero degrees, the imaging plane may angle from the surface of the subject 1106 to the right of the subject 1106. The image of the ultrasound device at the orientation 1108b illustrates an orientation in which the ultrasound device is perpendicular to the surface of the subject 1106. Thus, if the elevational steering angle from the ultrasound device is zero degrees, the imaging plane may extend from the surface of the subject 1106 perpendicular through the subject 1106. The image of the ultrasound device at the orientation 1108c illustrates an orientation in which the ultrasound device is angled from the surface of the subject 1106 to the right of the subject 1106. Thus, if the elevational steering angle from the ultrasound device is zero degrees, the imaging plane may angle from the surface of the subject 1106 to the left of the subject 1106.

The GUI 1100 may serve as an instruction to the user to fan an ultrasound device on a subject from an orientation corresponding to the image of the ultrasound device in the orientation 1108a, to an orientation corresponding to the image of the ultrasound device in the orientation 1108b, to an orientation corresponding to the image of the ultrasound device in the orientation 1108c. In other words, the GUI 1100 may serve as an instruction to the user to fan an ultrasound device on a subject such that the ultrasound device may collect multiple ultrasound images along multiple imaging planes relative to the subject 1106. In particular, the GUI 1100 may serve as an instruction to fan the ultrasound device such that it begins at an orientation angling from the surface of the subject 1106 to the left of the subject 1106, is moved to an orientation in which the ultrasound device is perpendicular to the surface of the subject 1106, and ends at an orientation angling from the surface of the subject 1106 to the right of the subject 1106. It should be appreciated that the instruction illustrated by the GUI 1100 is non-limiting and other forms for providing the instruction may also be used. For example, the instruction may be to fan the ultrasound device in an opposite direction from that illustrated in FIG. 11, such that the ultrasound device begins at an orientation angling from the surface of the subject 1106 to the right of the subject 1106 and ends at an orientation angling from the surface of the subject 1106 to the left of the subject 1106. Additionally, or alternatively, the GUI may illustrate more or fewer images of the ultrasound device than illustrated and/or more or fewer arrows than illustrated and/or may include the image of the icon 1026 illustrated in FIG. 13. The GUI 1100 may include video components, and the image and/or video may be stored on the processing device or on another device, such as a server, which the processing device may access.

Figure 12:
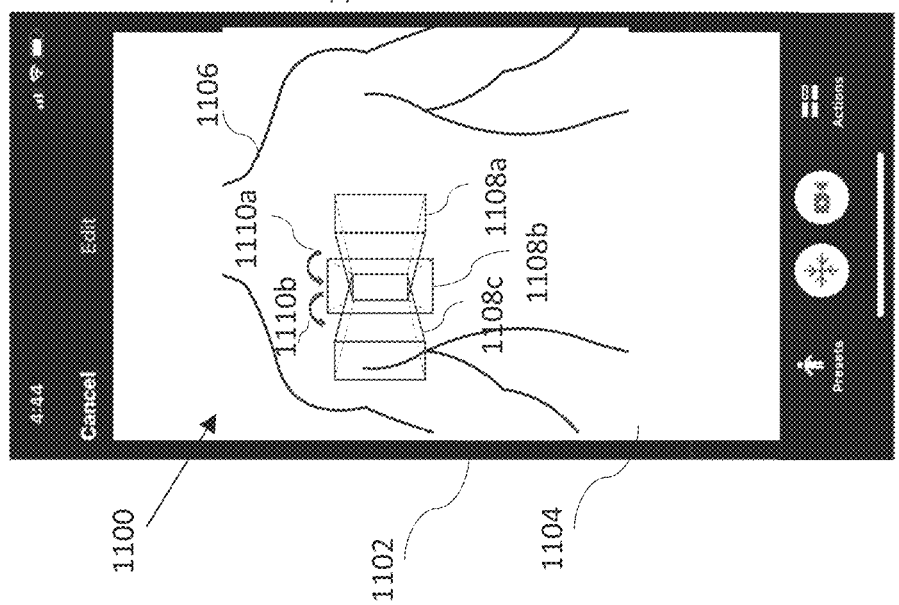
FIG. 12 illustrates an example instruction for instructing a user to collect multiple ultrasound images at multiple elevational steering angles, in accordance with certain embodiments described herein.

FIG. 12 illustrates an example instruction 1200 for instructing a user to collect multiple ultrasound images at multiple elevational steering angles, in accordance with certain embodiments described herein. The instruction 1200 is displayed on the display screen 1104 of the processing device 1102 (e.g., the processing device described with reference to the process 600). The instruction 1200 may be displayed in conjunction with acts 602 and/or 802. The instruction 1200 includes text instructing the user to fan the ultrasound device from the patient's left side to the patient's right side. Thus, the instruction 1200 may convey in text form what the GUI 1100 conveys in graphical form. It should be appreciated that the instruction 1200 is non-limiting and the text may be different than that displayed in FIG. 12 and/or the text may instruct the user to fan the ultrasound device from the patient's right side to the patient's left side. In some embodiments, both the GUI 1100 and the instruction 1200 may be displayed sequentially or simultaneously.

Figure 13:
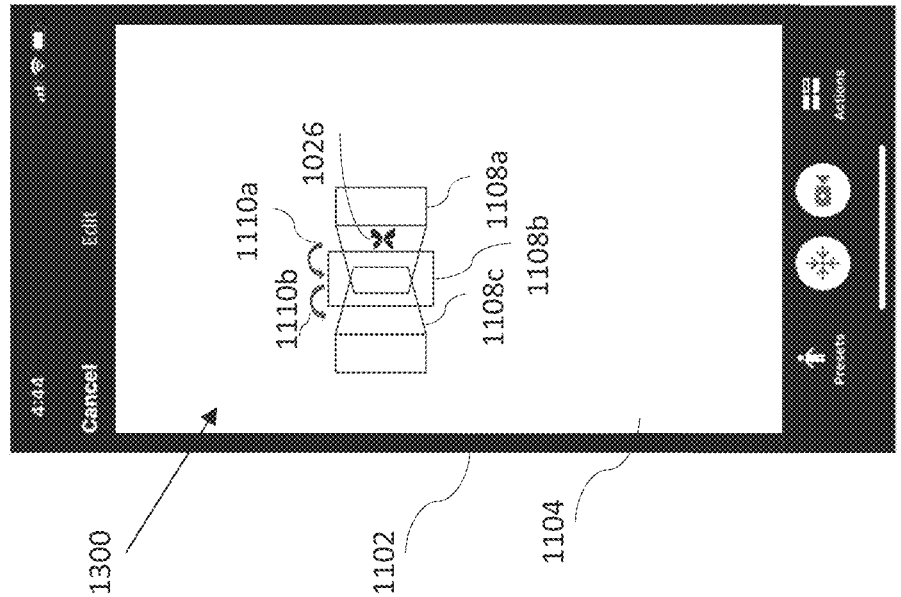
FIG. 13 illustrates an example GUI for instructing a user to collect multiple ultrasound images at multiple elevational steering angles, in accordance with certain embodiments described herein.

FIG. 13 illustrates an example GUI 1300 for instructing a user to collect multiple ultrasound images at multiple elevational steering angles, in accordance with certain embodiments described herein. The GUI 1300 is displayed on a display screen 1104 of a processing device 1102 (e.g., the processing device described with reference to the process 600). The GUI 1100 may be displayed in conjunction with acts 602 and/or 802. The GUI 1300 is the same as the GUI 1100, except that the GUI 1300 lacks the image of the subject 1106 and the image of the ultrasound device in the orientation 1108a includes an image of the icon 1026. The arrows 1110a and 1110b point in the same direction as the direction the icon 1026 is facing. Thus, the GUI 1300 may serve as an instruction to fan the ultrasound device in the direction of the icon 1026 on the ultrasound device. If, for example, the icon 1026 of the ultrasound device faces the right of the subject 1106, then the GUI 1300 may serve as an instruction to fan the ultrasound device from the left of the subject 1106 to the right of the subject 1106. It should be appreciated that the instruction illustrated by the GUI 1300 is non-limiting and other forms for providing the instruction may also be used. For example, the instruction may be to fan the ultrasound device in an opposite direction from that illustrated in FIG. 13, namely away from the direction of the icon 1026 on the ultrasound device. Additionally or alternatively, the GUI may illustrate more or fewer images of the ultrasound device than illustrated and/or more or fewer arrows than illustrated and/or may include the image of the subject 1106. The GUI 1300 may include video components, and the image and/or video may be stored on the processing device or on another device, such as a server, which the processing device may access.

Figure 14:
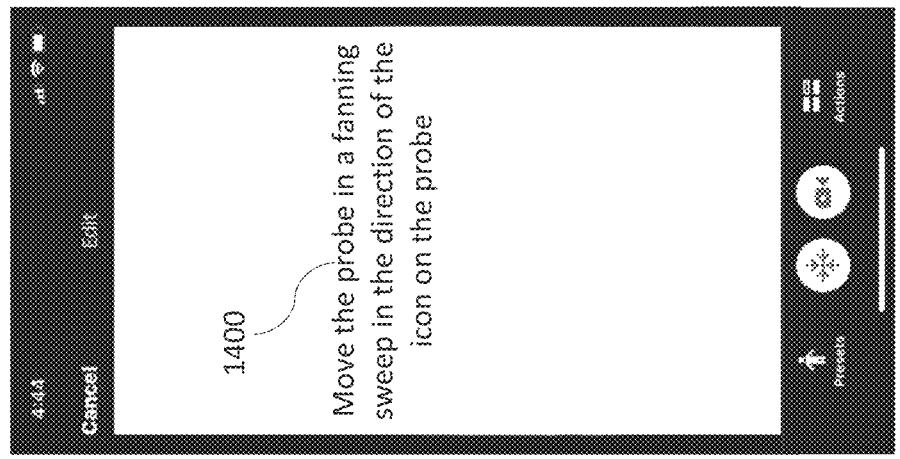
FIG. 14 illustrates an example instruction for instructing a user to collect multiple ultrasound images at multiple elevational steering angles, in accordance with certain embodiments described herein.

FIG. 14 illustrates an example instruction 1400 for instructing a user to collect multiple ultrasound images at multiple elevational steering angles, in accordance with certain embodiments described herein. The instruction 1400 is displayed on the display screen 1104 of the processing device 1102 (e.g., the processing device described with reference to the process 600). The instruction 1400 may be displayed in conjunction with acts 602 and/or 802. The instruction 1400 includes text instructing the user to fan the ultrasound device in the direction of the icon on the ultrasound device. Thus, the instruction 1400 may convey in text form what the GUI 1300 conveys in graphical form. It should be appreciated that the instruction 1400 is non-limiting and the text may be different than that displayed in FIG. 14 and/or the text may instruct the user to fan the ultrasound device away from the direction of the icon on the ultrasound device. In some embodiments, both the GUI 1300 and the instruction 1400 may be displayed sequentially or simultaneously.

FIG. 15 illustrates an example GUI 1500 for instructing a user to move the ultrasound device to continue to collect ultrasound images along the imaging plane at which an ultrasound image selected based on its quality was collected, in accordance with certain embodiments described herein. The GUI 1500 is displayed on the display screen 1104 of the processing device 1102 (e.g., the processing device described with reference to the process 600). The GUI 1500 may be displayed in conjunction with acts 606 and/or 706. The GUI 1500 includes the image of the subject 1106, the two images of the ultrasound device in the different orientations 1108*a* and 1108*b*, and the arrow 1110*a*. The arrow 1110*a* points from the image of the ultrasound device in the orientation 1108*a* to the image of the ultrasound device in the orientation 1108*b*. As described above, the processing device may monitor the current orientation of the ultrasound device (as determined by the orientation sensors) and provide instructions for fanning the ultrasound device such that its orientation becomes nearer to the orientation at which the ultrasound image selected based on its quality was collected. In the specific example of FIG. 15, the orientation at which the ultrasound image selected based on its quality was collected may be the orientation when the ultrasound device is perpendicular to the surface of the subject. However, based on the orientation sensors, the processing device may determine that the ultrasound device is angled towards the left of the subject. Thus, the processing device may provide the GUI 1500, which may serve as a general instruction that the ultrasound device is angling from the surface of the subject 1106 too far to the left of the subject 1106 and should be moved to an orientation in which the ultrasound device is more perpendicular to the surface of the subject 1106. In some embodiments, the GUI 1500 may be a stored image or video (stored on the processing device or stored on another device, such as a server, which the processing device may access) that the processing device may display upon determining that the ultrasound device is angling from the surface of the subject 1106 too far to the left of the subject 1106 and should be moved to an orientation in which the ultrasound device is more perpendicular to the surface of the subject 1106. The processing device may access other pre-stored images or videos when the ultrasound device needs to be moved in other directions.

In some embodiments, the GUI 1500 may serve as a more specific instruction; namely, the image of the ultrasound device in the orientation 1108*a* may depict the current orientation of the ultrasound device (which may be updated as the ultrasound device moves) and the image of the ultrasound device in the orientation 1108*b* may depict the target orientation of the ultrasound device. The images depicting the current and target orientations of the ultrasound device may be generated using pose estimation techniques, such as those described in U.S. patent application Ser. No. 16/734,888 titled "METHODS AND APPARATUSES FOR ULTRASOUND DATA COLLECTION," filed on Jan. 6, 2020 and published as US 2020/0214674 A1 (and assigned to the assignee of the instant application), the content of which is incorporated by reference herein in its entirety. It should be appreciated that the instruction illustrated by the GUI 1500 is non-limiting and other forms for providing the instruction may also be used. For example, the instruction may be to move the ultrasound device so that it angles more to the right of the subject 1106 or to move the ultrasound device so that it angles more to the left of the subject 1106.

FIG. 16 illustrates an example instruction 1600 for instructing a user to move the ultrasound device to continue to collect ultrasound images along the imaging plane at which an ultrasound image selected based on its quality was collected, in accordance with certain embodiments described herein. The instruction 1600 is displayed on the display screen 1104 of the processing device 1102 (e.g., the processing device described with reference to the process 600). The instruction 1600 may be displayed in conjunction with acts 606 and/or 706. The instruction 1600 includes text instructing the user to fan the ultrasound device to the right of the patient. Thus, the instruction 1600 may convey in text form what the GUI 1500 conveys in graphical form. It should be appreciated that the instruction 1600 is non-limiting and the text may be different than that displayed in FIG. 16 and/or the text may instruct the user to fan the ultrasound device to the left of the patient. In some embodiments, both the GUI 1500 and the instruction 1600 may be displayed sequentially or simultaneously.

Figures 17, 18:
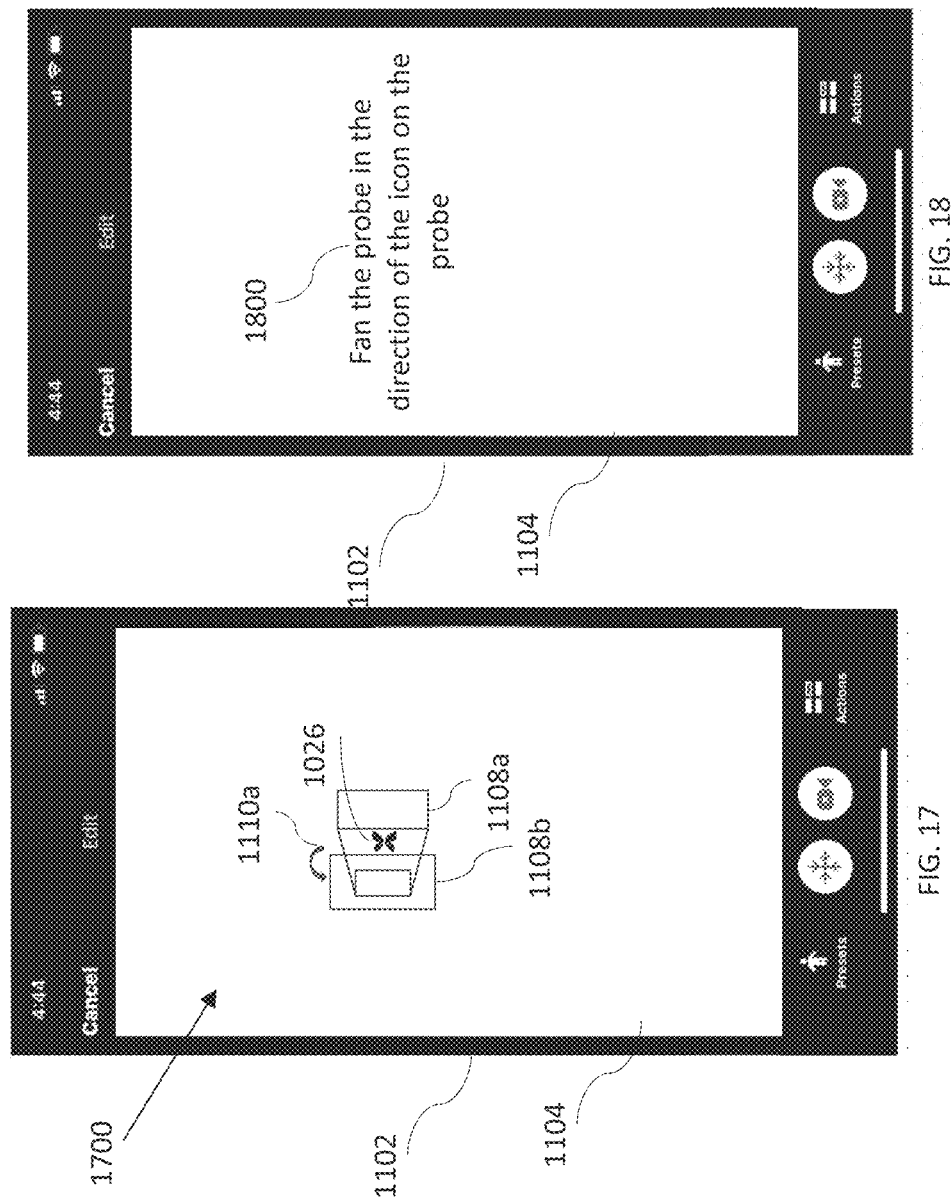
FIG. 17 illustrates an example GUI for instructing a user to move the ultrasound device to continue to collect ultrasound images along the imaging plane at which an ultrasound image selected based on its quality was collected, in accordance with certain embodiments described herein.
FIG. 18 illustrates an example instruction for instructing a user to move the ultrasound device to continue to collect ultrasound images along the imaging plane at which an ultrasound image selected based on its quality was collected, in accordance with certain embodiments described herein.

FIG. 17 illustrates an example GUI 1700 for instructing a user to move the ultrasound device to continue to collect ultrasound images along the imaging plane at which an ultrasound image selected based on its quality was collected, in accordance with certain embodiments described herein. The GUI 1700 is displayed on the display screen 1104 of the processing device 1102 (e.g., the processing device described with reference to the process 600). The GUI 1700 may be displayed in conjunction with acts 606 and/or 706. The GUI 1700 is the same as the GUI 1500, except that the GUI 1700 lacks the image of the subject 1106 and the image of the ultrasound device in the orientation 1108*a* includes an image of the icon 1026. The arrow 1110*a* points in the same direction as the direction the icon 1026 is facing. Thus, the GUI 1700 may serve as an instruction to fan the ultrasound device in the direction of the icon 1026 on the ultrasound device.

FIG. 18 illustrates an example instruction 1800 for instructing a user to move the ultrasound device to continue to collect ultrasound images along the imaging plane at which an ultrasound image selected based on its quality was collected, in accordance with certain embodiments described herein. The instruction 1800 is displayed on the display screen 1104 of the processing device 1102 (e.g., the processing device described with reference to the process 600). The instruction 1800 may be displayed in conjunction with acts 606 and/or 706. The instruction 1800 includes text instructing the user to fan the probe in the direction of the icon on the probe. Thus, the instruction 1800 may convey in text form what the GUI 1700 conveys in graphical form. It should be appreciated that the instruction 1800 is non-limiting and the text may be different than that displayed in FIG. 18 and/or the text may instruct the user to fan the ultrasound device away from the direction of the icon on the probe. In some embodiments, both the GUI 1700 and the instruction 1800 may be displayed sequentially or simultaneously.

FIG. 19 illustrates an example GUI 1900 for instructing a user to continue to collect ultrasound images along the imaging plane at which an ultrasound image selected based on its quality was collected, in accordance with certain embodiments described herein. The GUI 1900 is displayed on the display screen 1104 of the processing device 1102 (e.g., the processing device described with reference to the process 600). The GUI 1900 may be displayed in conjunction with acts 606 and/or 706. The GUI 1900 includes a left section 1912a, a center section 1912b, a right section 1912c, and a marker 1914. In the example of FIG. 19, the marker 1914 is in the left section 1912a. As described above, the processing device may monitor the current orientation of the ultrasound device (as determined by the orientation sensors) and provide instructions for fanning the ultrasound device such that its orientation becomes nearer to the orientation at which the ultrasound image selected based on its quality was collected. In the specific example of FIG. 19, based on the orientation sensors, the processing device may determine that the ultrasound device is angled too far towards the left of the subject, and thus in some embodiments the GUI 1900 may display the marker 1914 in the left section 1912a. Thus, the processing device may provide the GUI 1900, which may serve as a general instruction that the ultrasound device is angling from the surface of the subject 1106 too far to the left of the subject 1106. Alternatively, in some embodiments the GUI 1900 may function in the manner of a bubble level, such that the GUI 1900 may display the marker 1914 in the left section 1912a when the processing device determines that the ultrasound device is angled too far towards the right of the subject. Generally, the position of the marker 1914 within the left section 1912a, the center section 1912b, and/or the right section 1912c may be based on the current orientation of the ultrasound device relative to the subject. The processing device may update the location of the marker 1914 based on the current orientation of the ultrasound device relative to the subject as the user moves the ultrasound device. Thus, the marker 1914 is dynamic, being movable to correspond to a current location of the ultrasound device.

Figure 21:
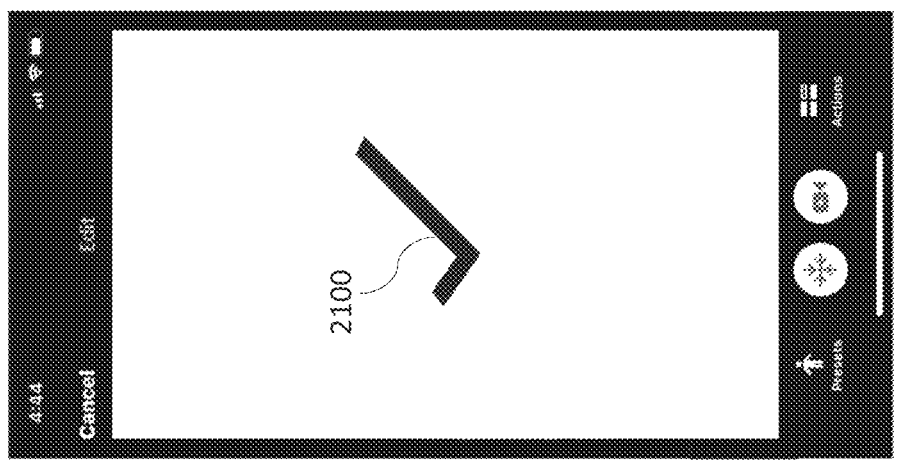
FIGS. 20 and 21 illustrate example graphical user interfaces for providing an indication once the current orientation of the ultrasound device is the same as the orientation at which the ultrasound image selected based on its quality was collected, in accordance with certain embodiments described herein.
Figure 20:
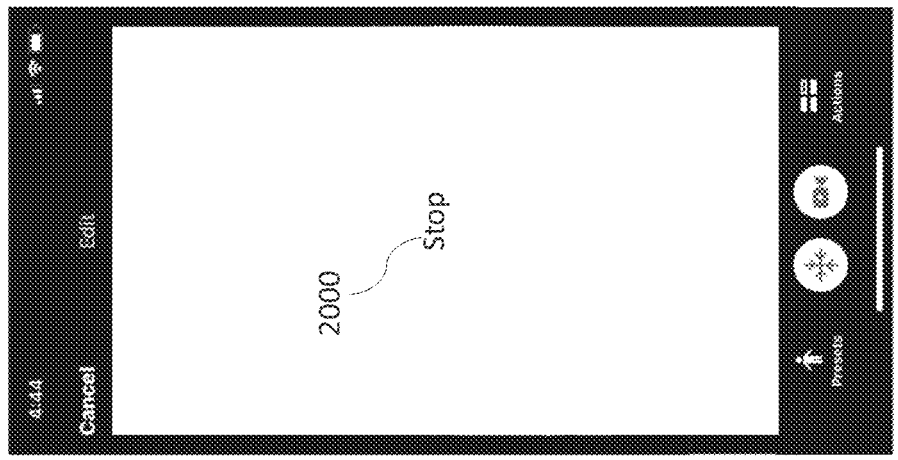

FIGS. 20 and 21 illustrate example graphical user interfaces (GUI) 2000 and 2100 for providing an indication once the current orientation of the ultrasound device is the same as the orientation at which the ultrasound image selected based on its quality was collected, in accordance with certain embodiments described herein. The GUIs 2000 and 2100 are displayed on the display screen 1104 of the processing device 1102 (e.g., the processing device described with reference to the process 600). The GUIs 2000 and 2100 may be displayed in conjunction with acts 606 and/or 706. In the GUI 2000, the indication is text 2000 ("Stop", although other texts may be used). In the GUI 2100, the indication is a symbol (a check mark, although other symbols may be used). Alternatively, the processing device may simply cease to display the GUI (e.g., the GUIs 1500, 1700, 1200, 1400, or 1900) that was previously providing instructions for moving the ultrasound device.

While the above description has described fanning the ultrasound device left to right relative to the subject 1106, the same methods and GUIs may be modified for fanning the ultrasound device up and down relative to the subject 1106.

In any of the preceding embodiments in which an ultrasound image is selected from among multiple ultrasound images based on its quality, the selected image(s) may be the image(s) having the highest quality from among the collected ultrasound images. In some embodiments, the selected image(s) may be the image(s) having a quality above a threshold quality, even if not the highest quality from among the collected ultrasound images. In some embodiments, the selected image(s) may be the image(s) having an acceptable quality level even if not the highest quality from among the collected ultrasound images. The quality may be assessed in any of the manners described previously herein.

Once the ultrasound device has been configured to continue to collect ultrasound images at a particular elevational steering angle and/or the user has been instructed to collect ultrasound images at a particular orientation relative to the subject (e.g., after acts 506, 606, 706, and/or 806), the ultrasound images may be used by a clinician (e.g., for diagnosis) and/or for automatic calculations (e.g., counting B-lines in ultrasound images of the lungs, calculating volume of a bladder, calculating ejection fraction from ultrasound images of the heart, etc.).

Figure 22:
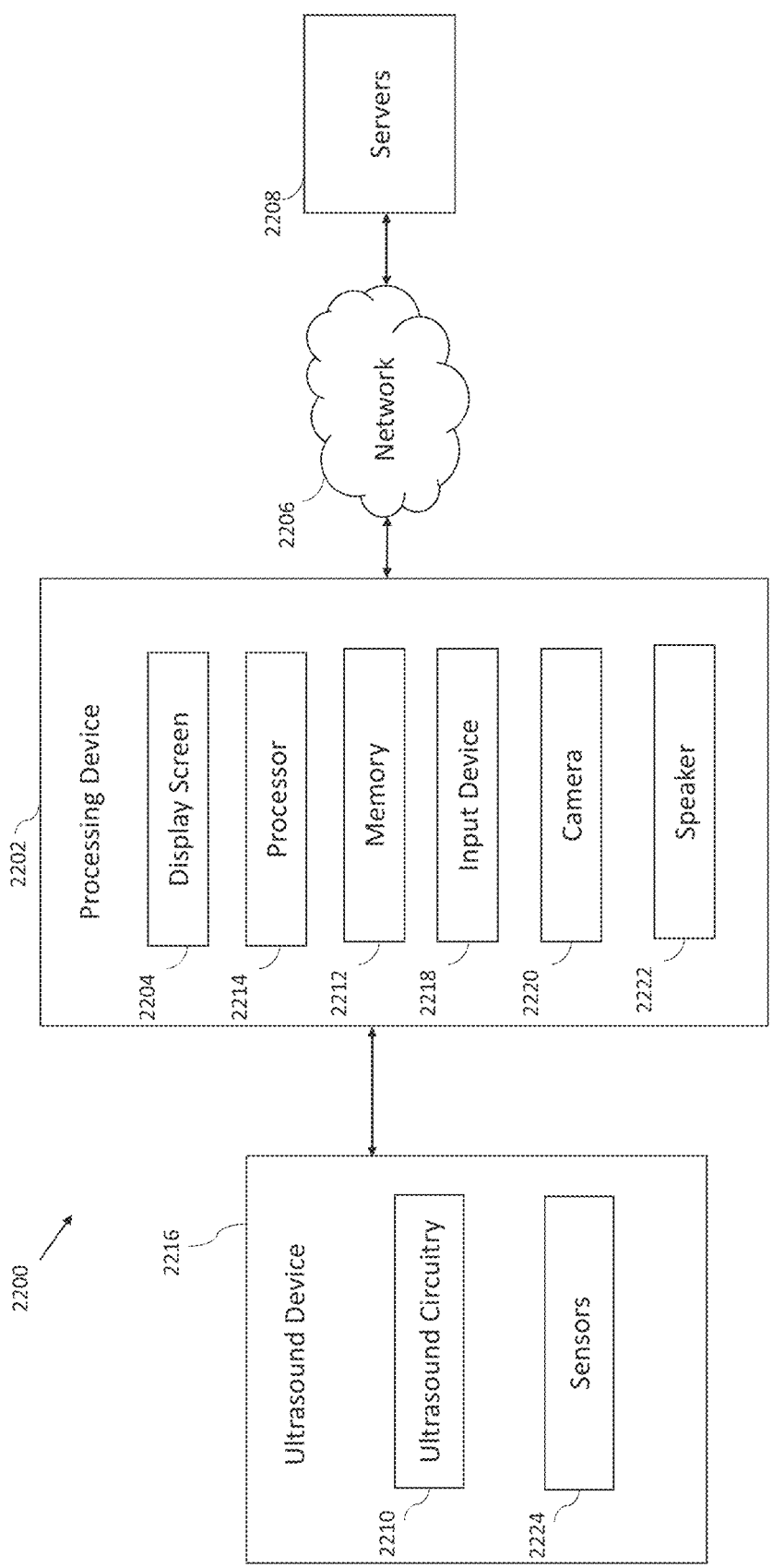
FIG. 22 illustrates a schematic block diagram of an example ultrasound system upon which various aspects of the technology described herein may be practiced.

FIG. 22 illustrates a schematic block diagram of an example ultrasound system 2200 upon which various aspects of the technology described herein may be practiced. The ultrasound system 2200 includes an ultrasound device 2216, a processing device 2202, a network 2206, and one or more servers 2208. The processing device 2202 may be any of the processing devices described herein (e.g., the processing device 1102). The ultrasound device 2216 may be any of the ultrasound devices described herein (e.g., the ultrasound device 116).

The ultrasound device 2216 includes ultrasound circuitry 2210 and sensor(s) 2224. The processing device 2202 includes a camera 2220, a display screen 2204, a processor 2214, a memory 2212, an input device 2218, and a speaker 2222. The processing device 2202 is in wired (e.g., through a lightning connector or a mini-USB connector) and/or wireless communication (e.g., using BLUETOOTH, ZIGBEE, and/or WiFi wireless protocols) with the ultrasound device 2216. The processing device 2202 is in wireless communication with the one or more servers 2208 over the network 2206, although wired connections are possible.

The ultrasound device 2216 may be configured to generate ultrasound data that may be employed to generate an ultrasound image. The ultrasound device 2216 may be constructed in any of a variety of ways. In some embodiments, the ultrasound device 2216 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound circuitry 2210 may be configured to generate the ultrasound data. The ultrasound circuitry 2210 may include one or more ultrasonic transducers monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed on the same chip as other electronic components in the ultrasound circuitry 2210 (e.g., transmit circuitry, receive circuitry, control circuitry, power management circuitry, and processing circuitry) to form a monolithic ultrasound device.

The sensor(s) 2224 (of which any of the orientation sensors described herein may be an example) may be configured to generate data regarding acceleration of the ultrasound device 2216, data regarding angular velocity of the ultrasound device 2216, and/or data regarding magnetic force acting on the ultrasound device 2216 due to the local magnetic field, which in many cases is simply the field of the earth. The sensor(s) 2224 may include an accelerometer, a gyroscope, and/or a magnetometer. Depending on the nature and number of the sensor(s) 2224, the data generated by the sensor(s) 2224 may describe three degrees of freedom, six degrees of freedom, or nine degrees of freedom for the ultrasound device 2216. For example, the sensor(s) 2224 may include an accelerometer, a gyroscope, and/or magnetometer. Each of these types of sensors may describe three degrees of freedom. If the sensor(s) 2224 includes one of these sensors, the sensor 2224 may describe three degrees of freedom. If the sensor(s) 2224 includes two of these sensors, the sensor(s) 2224 may describe two degrees of freedom. If the sensor(s) 2224 includes three of these sensors, the sensor(s) 2224 may describe nine degrees of freedom.

The ultrasound device 2216 may transmit ultrasound data and/or ultrasound images to the processing device 2202 over a wired (e.g., through a lightning connector or a mini-USB connector) and/or wireless (e.g., using BLUETOOTH, ZIGBEE, and/or WiFi wireless protocols) communication link.

Referring now to the processing device 2202, the processor 2214 may include specially-programmed and/or special-purpose hardware such as an application-specific integrated circuit (ASIC). For example, the processor 2214 may include one or more graphics processing units (GPUs) and/or one or more tensor processing units (TPUs). TPUs may be ASICs specifically designed for machine learning (e.g., deep learning). The TPUs may be employed, for example, to accelerate the inference phase of a neural network. The processing device 2202 may be configured to process the ultrasound data received from the ultrasound device 2216 to generate ultrasound images for display on the display screen 2204 (of which the display screen 1104 may be an example). The processing may be performed by, for example, the processor 2214. The processor 2214 may also be adapted to control the acquisition of ultrasound data with the ultrasound device 2216. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data may be sequentially displayed. Additionally, or alternatively, the ultrasound data may be stored temporarily in a buffer during a scanning session and processed in less than real-time.

The processing device 2202 may be configured to perform certain of the processes (e.g., the processes 500, 600, 700, and/or 800) described herein using the processor 2214 (e.g., one or more computer hardware processors) and one or more articles of manufacture that include non-transitory computer-readable storage media such as the memory 2212. The processor 2214 may control writing data to and reading data from the memory 2212 in any suitable manner. To perform certain of the processes described herein, the processor 2214 may execute one or more processor-executable instructions stored in one or more non-transitory computer-readable storage media (e.g., the memory 2212), which may serve as non-transitory computer-readable storage media storing processor-executable instructions for execution by the processor 2214. The camera 2220 may be configured to detect light (e.g., visible light) to form an image. The camera 2220 may be on the same face of the processing device 2202 as the display screen 2204. The display screen 2204 may be configured to display images and/or videos, and may be, for example, a liquid crystal display (LCD), a plasma display, and/or an organic light emitting diode (OLED) display on the processing device 2202. The input device 2218 may include one or more devices capable of receiving input from a user and transmitting the input to the processor 2214. For example, the input device 2218 may include a keyboard, a mouse, a microphone, touch-enabled sensors on the display screen 2204, and/or a microphone. The display screen 2204, the input device 2218, the camera 2220, and the speaker 2222 may be communicatively coupled to the processor 2214 and/or under the control of the processor 2214.

It should be appreciated that the processing device 2202 may be implemented in any of a variety of ways. For example, the processing device 2202 may be implemented as a handheld device such as a mobile smartphone or a tablet. Thereby, a user of the ultrasound device 2216 may be able to operate the ultrasound device 2216 with one hand and hold the processing device 2202 with another hand. In other examples, the processing device 2202 may be implemented as a portable device that is not a handheld device, such as a laptop. In yet other examples, the processing device 2202 may be implemented as a stationary device such as a desktop computer. The processing device 2202 may be connected to the network 2206 over a wired connection (e.g., via an Ethernet cable) and/or a wireless connection (e.g., over a WiFi network). The processing device 2202 may thereby communicate with (e.g., transmit data to or receive data from) the one or more servers 2208 over the network 2206. For example, a party may provide from the server 2208 to the processing device 2202 processor-executable instructions for storing in one or more non-transitory computer-readable storage media (e.g., the memory 2212) which, when executed, may cause the processing device 2202 to perform certain of the processes (e.g., the processes 500, 600, 700, and/or 800) described herein.

In those embodiments in which a statistical model is used, the statistical model may be a convolutional neural network, a fully connected neural network, a recurrent neural network (e.g., a long short-term memory (LSTM) recurrent neural network), a random forest, a support vector machine, or a linear classifier, and may use deep learning techniques to generate the segmented anatomical portions.

In some embodiments in which a statistical model is used, a neural network is used and has one or more convolution layers to form a convolutional neural network. An example convolutional neural network is shown in FIG. 14 of U.S. Pat. No. 10,993,697 B2, filed on Jun. 19, 2017 and incorporated by reference herein in its entirety. The convolutional neural network comprises an input layer to receive an image, an output layer to provide the output, and a plurality of hidden layers connected between the input layer and the output layer. The plurality of hidden layers comprises convolution and pooling layers and dense layers.

The input layer may receive the input to the convolutional neural network. The input may be an ultrasound image of the types described herein.

The input layer may be followed by one or more convolution and pooling layers. A convolutional layer may comprise a set of filters that are spatially smaller (e.g., have a smaller width and/or height) than the input to the convolutional layer (e.g., the image). Each of the filters may be convolved with the input to the convolutional layer to produce an activation map (e.g., a 2-dimensional activation map) indicative of the responses of that filter at every spatial position. The convolutional layer may be followed by a pooling layer that down-samples the output of a convolutional layer to reduce its dimensions. The pooling layer may use any of a variety of pooling techniques such as max pooling and/or global average pooling. In some embodiments, the down-sampling may be performed by the convolution layer itself (e.g., without a pooling layer) using striding.

The convolution and pooling layers may be followed by dense layers. The dense layers may comprise one or more layers each with one or more neurons that receives an input from a previous layer (e.g., a convolutional or pooling layer) and provides an output to a subsequent layer (e.g., the output layer). The dense layers may be described as "dense" because each of the neurons in a given layer may receive an input from each neuron in a previous layer and provide an output to each neuron in a subsequent layer. The dense layers may be followed by an output layer that provides the output of the convolutional neural network. The output may be, for example, an indication of which class, from a set of classes, the image (or any portion of the image) belongs to.

It should be appreciated that the convolutional neural network described is only one example implementation and that other implementations may be employed. For example, one or more layers may be added to or removed from the convolutional neural network. Additional example layers that may be added to the convolutional neural network include: a rectified linear units (ReLU) layer, a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

Convolutional neural networks may be employed to perform any of a variety of functions described herein. For example, a convolutional neural networks may be employed to: (1) identify an anatomical view contained in an ultrasound image, (2) identify an instruction to provide an operator, (3) identify an anatomical feature in an ultrasound image, or (4) identify a pose of ultrasound device. It should be appreciated that more than a single convolutional neural network may be employed to perform one or more of the functions described herein.

According to an aspect of the present disclosure, an apparatus is provided, comprising a processing device in operative communication with an ultrasound device. The processing device is configured to: instruct a user to collect multiple ultrasound images at multiple orientations relative to a subject; select an ultrasound image of the multiple ultrasound images based on its quality; and instruct the user to continue to collect ultrasound images by moving the ultrasound device to an orientation of the multiple orientations relative to the subject at which the ultrasound image selected based on its quality was collected.

In some embodiments, the processing device is configured, when instructing the user to collect the multiple ultrasound images at the multiple orientations relative to the subject, to instruct the user to fan the ultrasound device on the subject. When instructing the user to fan the ultrasound device on the subject, to instruct the user to move the ultrasound device in a short axis of an ultrasound transducer array of the ultrasound device approximately about a fixed point on the subject while changing an angle of insonation relative to the subject away from 90 degrees.

In some embodiments, the processing device is configured to configure the ultrasound device to use a constant elevational steering angle when collecting the multiple ultrasound images at the multiple orientations relative to the subject.

In some embodiments, the processing device is further configured to collect data regarding an orientation of the ultrasound device from one or more orientation sensors of the ultrasound device when each of the multiple ultrasound images is collected. The processing device may be further configured to store each of the multiple ultrasound images along with an indication of data regarding an orientation of the ultrasound device used for collecting each of the multiple ultrasound images. The processing device may be configured, when instructing the user to continue to collect ultrasound images by moving the ultrasound device to the orientation of the multiple orientations relative to the subject at which the ultrasound image selected based on its was collected, to determine the orientation at which the ultrasound image selected based on its was collected based on an indication stored along with this ultrasound image.

In some embodiments, the processing device is configured, when selecting the ultrasound image of the multiple ultrasound images based on its quality, to determine the quality of the selected ultrasound image by calculating a prediction of a collective opinion of a group of individuals regarding the clinical usability of the selected ultrasound image.

In some embodiments, the processing device is configured, when selecting the ultrasound image of the multiple ultrasound images based on its quality, to determine the quality of the selected ultrasound image by determining a presence or absence of landmarks in the selected ultrasound image.

In some embodiments, the processing device is configured, when selecting the ultrasound image of the multiple ultrasound images based on its quality, to determine the quality of the selected ultrasound image by determining a quality of one or more landmarks in the selected ultrasound image. The selected ultrasound image may be an image of lungs, and the quality of the one or more landmarks is related to a height of a pleural line in the selected ultrasound image.

In some embodiments, the processing device is configured, when selecting the ultrasound image of the multiple ultrasound images based on its quality, to determine the quality of the selected ultrasound image by using a statistical model.

In some embodiments, the processing device is configured, when instructing the user to continue to collect ultrasound images by moving the ultrasound device to the orientation of the multiple orientations relative to the subject at which the ultrasound image selected based on its was collected, to monitor a current orientation of the ultrasound device based on orientation sensors of the ultrasound device and instruct the user to fan the ultrasound device such that its orientation becomes nearer to the orientation of the multiple orientations relative to the subject at which the ultrasound image selected based on its quality was collected. The processing device may further be configured, when instructing the user to fan the ultrasound device such that its orientation becomes nearer to the orientation of the multiple orientations relative to the subject at which the ultrasound image selected based on its quality was collected, to cease to instruct the user to fan the ultrasound device or to instruct the user to stop fanning the ultrasound device once the ultrasound device is at the orientation of the multiple orientations relative to the subject at which the ultrasound image selected based on its quality was collected.

In some embodiments, the processing device is configured, when instructing the user to collect the multiple ultrasound images at the multiple orientations relative to the subject, to display a graphical user interface comprising an image of a subject and multiple images of an ultrasound device in different orientations relative to the image of the subject.

In some embodiments, the processing device is configured, when instructing the user to continue to collect ultrasound images at the orientation of the multiple orientations relative to the subject at which the ultrasound image selected based on its quality was collected, to display a graphical user interface comprising an image of a subject and multiple images of an ultrasound device in different orientations relative to the image of the subject.

In some embodiments, the processing device is configured, when instructing the user to continue to collect ultrasound images at the orientation of the multiple orientations relative to the subject at which the ultrasound image selected based on its quality was collected, to display a graphical user interface comprising a left section, a center section, a right section, and a marker having a position within the left section, the center section, and/or the right section corresponding to a current orientation of the ultrasound device relative to the subject. The graphical user interface may be configured to operate as a bubble level.

According to an aspect of the present disclosure, a method is provided, comprising instructing, with a processing device in operative communication with an ultrasound device, a user to collect multiple ultrasound images at multiple orientations relative to a subject using the ultrasound device; selecting, with the processing device, an ultrasound image of the multiple ultrasound images based on its quality; and instructing, with the processing device, the user to continue to collect ultrasound images by moving the ultrasound device to an orientation of the multiple orientations relative to the subject at which the ultrasound image selected based on its quality was collected.

In some embodiments, instructing the user to collect the multiple ultrasound images at the multiple orientations relative to the subject comprises instructing the user to fan the ultrasound device on the subject. Instructing the user to fan the ultrasound device on the subject comprises instructing the user to move the ultrasound device in a short axis of an ultrasound transducer array of the ultrasound device approximately about a fixed point on the subject while changing an angle of insonation relative to the subject away from 90 degrees.

In some embodiments, configuring, with the processing device, the ultrasound device to use a constant elevational steering angle when collecting the multiple ultrasound images at the multiple orientations relative to the subject.

In some embodiments, collecting, with the processing device, data regarding an orientation of the ultrasound device from one or more orientation sensors of the ultrasound device when each of the multiple ultrasound images is collected. Storing, with the processing device, each of the multiple ultrasound images along with an indication of data regarding an orientation of the ultrasound device used for collecting each of the multiple ultrasound images. Instructing the user to continue to collect ultrasound images by moving the ultrasound device to the orientation of the multiple orientations relative to the subject at which the ultrasound image selected based on its was collected comprises determining the orientation at which the ultrasound image selected based on its was collected based on an indication stored along with this ultrasound image.

In some embodiments, selecting the ultrasound image of the multiple ultrasound images based on its quality comprises determining the quality of the selected ultrasound image by calculating a prediction of a collective opinion of a group of individuals regarding the clinical usability of the selected ultrasound image.

In some embodiments, selecting the ultrasound image of the multiple ultrasound images based on its quality comprises determining the quality of the selected ultrasound image by determining a presence or absence of landmarks in the selected ultrasound image.

In some embodiments, selecting the ultrasound image of the multiple ultrasound images based on its quality comprises determining the quality of the selected ultrasound image by determining a quality of one or more landmarks in the selected ultrasound image. The selected ultrasound image may be an image of lungs, and wherein determining the quality of the one or more landmarks comprises determining a quality based on a height of a pleural line in the selected ultrasound image.

In some embodiments, selecting the ultrasound image of the multiple ultrasound images based on its quality comprises determining the quality of the selected ultrasound image by using a statistical model.

In some embodiments, when instructing the user to continue to collect ultrasound images by moving the ultrasound device to the orientation of the multiple orientations relative to the subject at which the ultrasound image selected based on its was collected, monitoring a current orientation of the ultrasound device based on orientation sensors of the ultrasound device and instructing the user to fan the ultrasound device such that its orientation becomes nearer to the orientation of the multiple orientations relative to the subject at which the ultrasound image selected based on its quality was collected. Ceasing instruction to the user to fan the ultrasound device or instructing the user to stop fanning the ultrasound device once the ultrasound device is at the orientation of the multiple orientations relative to the subject at which the ultrasound image selected based on its quality was collected.

In some embodiments, when instructing the user to collect the multiple ultrasound images at the multiple orientations relative to the subject, displaying a graphical user interface comprising an image of a subject and multiple images of an ultrasound device in different orientations relative to the image of the subject.

In some embodiments, when instructing the user to continue to collect ultrasound images at the orientation of the multiple orientations relative to the subject at which the ultrasound image selected based on its quality was collected, displaying a graphical user interface comprising an image of a subject and multiple images of an ultrasound device in different orientations relative to the image of the subject.

In some embodiments, when instructing the user to continue to collect ultrasound images at the orientation of the multiple orientations relative to the subject at which the ultrasound image selected based on its quality was collected, a graphical user interface is displayed comprising a left section, a center section, a right section, and a marker having a position within the left section, the center section, and/or the right section corresponding to a current orientation of the ultrasound device relative to the subject. Additionally, the graphical user interface may be operated as a bubble level.

According an aspect of the present disclosure, at least one non-transitory computer-readable storage medium storing processor-executable instructions is provided that, when executed by at least one processor on a processing device in operative communication with an ultrasound device, cause the processing device to instruct a user of the ultrasound device to collect multiple ultrasound images at multiple orientations relative to a subject; select an ultrasound image of the multiple ultrasound images based on its quality; and instruct the user to continue to collect ultrasound images by moving the ultrasound device to an orientation of the multiple orientations relative to the subject at which the ultrasound image selected based on its quality was collected.

In some embodiments, the processor-executable instructions, when executed by the at least one processor, cause the processing device, when instructing the user to collect the multiple ultrasound images at the multiple orientations relative to the subject, to instruct the user to fan the ultrasound device on the subject. When instructing the user to fan the ultrasound device on the subject, to instruct the user to move the ultrasound device in a short axis of an ultrasound transducer array of the ultrasound device approximately about a fixed point on the subject while changing an angle of insonation relative to the subject away from 90 degrees.

In some embodiments, the processor-executable instructions, when executed by the at least one processor, cause the processing device to configure the ultrasound device to use a constant elevational steering angle when collecting the multiple ultrasound images at the multiple orientations relative to the subject.

In some embodiments, the processor-executable instructions, when executed by the at least one processor, cause the processing device to collect data regarding an orientation of the ultrasound device from one or more orientation sensors of the ultrasound device when each of the multiple ultrasound images is collected. The processor-executable instructions, when executed by the at least one processor, cause the processing device to store each of the multiple ultrasound images along with an indication of data regarding an orientation of the ultrasound device used for collecting each of the multiple ultrasound images. The processing device, when instructing the user to continue to collect ultrasound images by moving the ultrasound device to the orientation of the multiple orientations relative to the subject at which the ultrasound image selected based on its was collected, to determine the orientation at which the ultrasound image selected based on its was collected based on an indication stored along with this ultrasound image.

In some embodiments, the processor-executable instructions, when executed by the at least one processor, cause the processing device, when selecting the ultrasound image of the multiple ultrasound images based on its quality, to determine the quality of the selected ultrasound image by calculating a prediction of a collective opinion of a group of individuals regarding the clinical usability of the selected ultrasound image.

In some embodiments, the processor-executable instructions, when executed by the at least one processor, cause the processing device, when selecting the ultrasound image of the multiple ultrasound images based on its quality, to determine the quality of the selected ultrasound image by determining a presence or absence of landmarks in the selected ultrasound image.

In some embodiments, the processor-executable instructions, when executed by the at least one processor, cause the processing device, when selecting the ultrasound image of the multiple ultrasound images based on its quality, to determine the quality of the selected ultrasound image by determining a quality of one or more landmarks in the selected ultrasound image. The selected ultrasound image may be an image of lungs, and the quality of the one or more landmarks is related to a height of a pleural line in the selected ultrasound image.

In some embodiments, the processor-executable instructions, when executed by the at least one processor, cause the processing device, when selecting the ultrasound image of the multiple ultrasound images based on its quality, to determine the quality of the selected ultrasound image by using a statistical model.

In some embodiments, the processor-executable instructions, when executed by the at least one processor, cause the processing device, when instructing the user to continue to collect ultrasound images by moving the ultrasound device to the orientation of the multiple orientations relative to the subject at which the ultrasound image selected based on its was collected, to monitor a current orientation of the ultrasound device based on orientation sensors of the ultrasound device and instruct the user to fan the ultrasound device such that its orientation becomes nearer to the orientation of the multiple orientations relative to the subject at which the ultrasound image selected based on its quality was collected.

In some embodiments, the processor-executable instructions, when executed by the at least one processor, cause the processing device, when instructing the user to fan the ultrasound device such that its orientation becomes nearer to the orientation of the multiple orientations relative to the subject at which the ultrasound image selected based on its quality was collected, to cease to instruct the user to fan the ultrasound device or to instruct the user to stop fanning the ultrasound device once the ultrasound device is at the orientation of the multiple orientations relative to the subject at which the ultrasound image selected based on its quality was collected.

In some embodiments, the processor-executable instructions, when executed by the at least one processor, cause the processing device, when instructing the user to collect the multiple ultrasound images at the multiple orientations relative to the subject, to display a graphical user interface comprising an image of a subject and multiple images of an ultrasound device in different orientations relative to the image of the subject.

In some embodiments, the processor-executable instructions, when executed by the at least one processor, cause the processing device, when instructing the user to continue to collect ultrasound images at the orientation of the multiple orientations relative to the subject at which the ultrasound image selected based on its quality was collected, to display a graphical user interface comprising an image of a subject and multiple images of an ultrasound device in different orientations relative to the image of the subject.

In some embodiments, the processor-executable instructions, when executed by the at least one processor, cause the processing device, when instructing the user to continue to collect ultrasound images at the orientation of the multiple orientations relative to the subject at which the ultrasound image selected based on its quality was collected, to display a graphical user interface comprising a left section, a center section, a right section, and a marker having a position within the left section, the center section, and/or the right section corresponding to a current orientation of the ultrasound device relative to the subject. The graphical user interface may be configured to operate as a bubble level.

According to an aspect of the present disclosure, an apparatus is provided, comprising a processing device in operative communication with an ultrasound device, the processing device is configured to configure the ultrasound device to collect multiple ultrasound images from a subject at multiple elevational steering angles; select an ultrasound image of the multiple ultrasound images based on its quality; and instruct a user to continue to collect ultrasound images by moving the ultrasound device to an orientation relative to the subject corresponding to an elevational steering angle at which the ultrasound image selected based on its quality was collected.

In some embodiments, the processing device is configured, when configuring the ultrasound device to collect the multiple ultrasound images from the subject at the multiple elevational steering angles, to configure the ultrasound device to use beamforming. The processing device is configured, when configuring the ultrasound device to use beamforming, to configure ultrasound circuitry in the ultrasound device to apply different delays to transmitted and/or received ultrasound signals from different portions of an ultrasound transducer array of the ultrasound device.

In some embodiments, the processing device is further configured to store each of the multiple ultrasound images along with an indication of an elevational steering angle used for collecting each of the multiple ultrasound images. The processing device is configured, when instructing the user to continue to collect the ultrasound images by moving the ultrasound device to the orientation relative to the subject corresponding to the elevational steering angle at which the ultrasound image selected based on its quality was collected, to determine the elevational steering angle at which the ultrasound image selected based on its quality was collected based on an indication stored along with this ultrasound image.

In some embodiments, the processing device is configured, when selecting the ultrasound image of the multiple ultrasound images based on its quality, to determine the quality of the selected ultrasound image by calculating a prediction of a collective opinion of a group of individuals regarding the clinical usability of the selected ultrasound image.

In some embodiments, the processing device is configured, when selecting the ultrasound image of the multiple ultrasound images based on its quality, to determine the quality of the selected ultrasound image by determining a presence or absence of landmarks in the selected ultrasound image.

In some embodiments, the processing device is configured, when selecting the ultrasound image of the multiple ultrasound images based on its quality, to determine the quality of the selected ultrasound image by determining a quality of one or more landmarks in the selected ultrasound image. The selected ultrasound image may be an image of lungs, and the quality of the one or more landmarks is related to a height of a pleural line in the selected ultrasound image.

In some embodiments, the processing device is configured, when selecting the ultrasound image of the multiple ultrasound images based on its quality, to determine the quality of the selected ultrasound image by using a statistical model.

In some embodiments, the processing device is configured, when instructing the user to continue to collect the ultrasound images by moving the ultrasound device to the orientation relative to the subject corresponding to the elevational steering angle at which the ultrasound image selected based on its quality was collected, to monitor a current orientation of the ultrasound device based on orientation sensors of the ultrasound device and instruct the user to fan the ultrasound device such that its orientation becomes nearer to the orientation relative to the subject corresponding to the elevational steering angle at which the ultrasound image selected based on its quality was collected. The processing device is configured, when instructing the user to fan the ultrasound device such that its orientation becomes nearer to the orientation relative to the subject corresponding to the elevational steering angle at which the ultrasound image selected based on its quality was collected, to cease to instruct the user to fan the ultrasound device or to instruct the user to stop fanning the ultrasound device once the ultrasound device is at the orientation relative to the subject corresponding to the elevational steering angle at which the ultrasound image selected based on its quality was collected.

In some embodiments, the processing device is configured, when instructing the user to continue to collect the ultrasound images by moving the ultrasound device to the orientation relative to the subject corresponding to the elevational steering angle at which the ultrasound image selected based on its quality was collected, to display a graphical user interface comprising an image of a subject and multiple images of an ultrasound device in different orientations relative to the image of the subject.

In some embodiments, the processing device is configured, when instructing the user to continue to collect the ultrasound images by moving the ultrasound device to the orientation relative to the subject corresponding to the elevational steering angle at which the ultrasound image selected based on its quality was collected, to display a graphical user interface comprising a left section, a center section, a right section, and a marker having a position within the left section, the center section, and/or the right section corresponding to a current orientation of the ultrasound device relative to the subject. The graphical user interface may be configured to operate as a bubble level.

In some embodiments, the processing device is configured, when configuring the ultrasound device to collect the multiple ultrasound images at the multiple elevational steering angles, to configure the ultrasound device to collect between or equal to approximately 4-50 ultrasound images.

According to an aspect of the present disclosure, a method is provided, comprising configuring, with a processing device in operative communication with an ultrasound device, the ultrasound device to collect multiple ultrasound images from a subject at multiple elevational steering angles; selecting, with the processing device, an ultrasound image of the multiple ultrasound images based on its quality; and instructing, with the processing device, a user to continue to collect ultrasound images by moving the ultrasound device to an orientation relative to the subject corresponding to an elevational steering angle at which the ultrasound image selected based on its quality was collected.

In some embodiments, configuring the ultrasound device to collect the multiple ultrasound images from the subject at the multiple elevational steering angles comprises configuring the ultrasound device to use beamforming. Configuring the ultrasound device to use beamforming comprises configuring ultrasound circuitry in the ultrasound device to apply different delays to transmitted and/or received ultrasound signals from different portions of an ultrasound transducer array of the ultrasound device.

In some embodiments, storing each of the multiple ultrasound images along with an indication of an elevational steering angle used for collecting each of the multiple ultrasound images. When instructing the user to continue to collect the ultrasound images by moving the ultrasound device to the orientation relative to the subject corresponding to the elevational steering angle at which the ultrasound image selected based on its quality was collected, determining the elevational steering angle at which the ultrasound image selected based on its quality was collected based on an indication stored along with this ultrasound image.

In some embodiments, selecting the ultrasound image of the multiple ultrasound images based on its quality comprises determining the quality of the selected ultrasound image by calculating a prediction of a collective opinion of a group of individuals regarding the clinical usability of the selected ultrasound image.

In some embodiments, selecting the ultrasound image of the multiple ultrasound images based on its quality comprises determining the quality of the selected ultrasound image by determining a presence or absence of landmarks in the selected ultrasound image.

In some embodiments, selecting the ultrasound image of the multiple ultrasound images based on its quality comprises determining the quality of the selected ultrasound image by determining a quality of one or more landmarks in the selected ultrasound image. The selected ultrasound image may be an image of lungs, and the quality of the one or more landmarks is related to a height of a pleural line in the selected ultrasound image.

In some embodiments, selecting the ultrasound image of the multiple ultrasound images based on its quality comprises determining the quality of the selected ultrasound image by using a statistical model.

In some embodiments, when instructing the user to continue to collect the ultrasound images by moving the ultrasound device to the orientation relative to the subject corresponding to the elevational steering angle at which the ultrasound image selected based on its quality was collected, a current orientation of the ultrasound device is monitored based on orientation sensors of the ultrasound device and the user is instructed to fan the ultrasound device such that its orientation becomes nearer to the orientation relative to the subject corresponding to the elevational steering angle at which the ultrasound image selected based on its quality was collected. The method further comprises ceasing to instruct the user to fan the ultrasound device or instructing the user to stop fanning the ultrasound device once the ultrasound device is at the orientation relative to the subject corresponding to the elevational steering angle at which the ultrasound image selected based on its quality was collected.

In some embodiments, when instructing the user to continue to collect the ultrasound images by moving the ultrasound device to the orientation relative to the subject corresponding to the elevational steering angle at which the ultrasound image selected based on its quality was collected, displaying a graphical user interface comprising an image of a subject and multiple images of an ultrasound device in different orientations relative to the image of the subject.

In some embodiments, when instructing the user to continue to collect the ultrasound images by moving the ultrasound device to the orientation relative to the subject corresponding to the elevational steering angle at which the ultrasound image selected based on its quality was collected, displaying a graphical user interface comprising a left section, a center section, a right section, and a marker having a position within the left section, the center section, and/or the right section corresponding to a current orientation of the ultrasound device relative to the subject. The graphical user interface may operate as a bubble level.

In some embodiments, configuring the ultrasound device to collect the multiple ultrasound images at the multiple elevational steering angles comprises configuring the ultrasound device to collect between or equal to approximately 4-50 ultrasound images.

According to an aspect of the present disclosure, at least one non-transitory computer-readable storage medium storing processor-executable instructions is provided that, when executed by at least one processor on a processing device in operative communication with an ultrasound device, cause the processing device to configure the ultrasound device to collect multiple ultrasound images from a subject at multiple elevational steering angles; select an ultrasound image of the multiple ultrasound images based on its quality; and instruct a user to continue to collect ultrasound images by moving the ultrasound device to an orientation relative to the subject corresponding to an elevational steering angle at which the ultrasound image selected based on its quality was collected.

In some embodiments, the processor-executable instructions, when executed by the at least one processor, cause the processing device, when configuring the ultrasound device to collect the multiple ultrasound images from the subject at the multiple elevational steering angles, to configure the ultrasound device to use beamforming. The processor-executable instructions, when executed by the at least one processor, cause the processing device, when configuring the ultrasound device to use beamforming, to configure ultrasound circuitry in the ultrasound device to apply different delays to transmitted and/or received ultrasound signals from different portions of an ultrasound transducer array of the ultrasound device.

In some embodiments, the processor-executable instructions, when executed by the at least one processor, cause the processing device to store each of the multiple ultrasound images along with an indication of an elevational steering angle used for collecting each of the multiple ultrasound images. The processor-executable instructions, when executed by the at least one processor, cause the processing device, when instructing the user to continue to collect the ultrasound images by moving the ultrasound device to the orientation relative to the subject corresponding to the elevational steering angle at which the ultrasound image selected based on its quality was collected, to determine the elevational steering angle at which the ultrasound image selected based on its quality was collected based on an indication stored along with this ultrasound image.

In some embodiments, the processor-executable instructions, when executed by the at least one processor, cause the processing device, when selecting the ultrasound image of the multiple ultrasound images based on its quality, to determine the quality of the selected ultrasound image by calculating a prediction of a collective opinion of a group of individuals regarding the clinical usability of the selected ultrasound image.

In some embodiments, the processor-executable instructions, when executed by the at least one processor, cause the processing device, when selecting the ultrasound image of the multiple ultrasound images based on its quality, to determine the quality of the selected ultrasound image by determining a presence or absence of landmarks in the selected ultrasound image.

In some embodiments, the processor-executable instructions, when executed by the at least one processor, cause the processing device, when selecting the ultrasound image of the multiple ultrasound images based on its quality, to determine the quality of the selected ultrasound image by determining a quality of one or more landmarks in the selected ultrasound image. The selected ultrasound image may be an image of lungs, and the quality of the one or more landmarks is related to a height of a pleural line in the selected ultrasound image.

In some embodiments, the processor-executable instructions, when executed by the at least one processor, cause the processing device, when selecting the ultrasound image of the multiple ultrasound images based on its quality, to determine the quality of the selected ultrasound image by using a statistical model.

In some embodiments, the processor-executable instructions, when executed by the at least one processor, cause the processing device, when instructing the user to continue to collect the ultrasound images by moving the ultrasound device to the orientation relative to the subject corresponding to the elevational steering angle at which the ultrasound image selected based on its quality was collected, to monitor a current orientation of the ultrasound device based on orientation sensors of the ultrasound device and instruct the user to fan the ultrasound device such that its orientation becomes nearer to the orientation relative to the subject corresponding to the elevational steering angle at which the ultrasound image selected based on its quality was collected. The processor-executable instructions, when executed by the at least one processor, cause the processing device, when instructing the user to fan the ultrasound device such that its orientation becomes nearer to the orientation relative to the subject corresponding to the elevational steering angle at which the ultrasound image selected based on its quality was collected, to cease to instruct the user to fan the ultrasound device or to instruct the user to stop fanning the ultrasound device once the ultrasound device is at the orientation relative to the subject corresponding to the elevational steering angle at which the ultrasound image selected based on its quality was collected.

In some embodiments, the processor-executable instructions, when executed by the at least one processor, cause the processing device, when instructing the user to continue to collect the ultrasound images by moving the ultrasound device to the orientation relative to the subject corresponding to the elevational steering angle at which the ultrasound image selected based on its quality was collected, to display a graphical user interface comprising an image of a subject and multiple images of an ultrasound device in different orientations relative to the image of the subject.

In some embodiments, the processor-executable instructions, when executed by the at least one processor, cause the processing device, when instructing the user to continue to collect the ultrasound images by moving the ultrasound device to the orientation relative to the subject corresponding to the elevational steering angle at which the ultrasound image selected based on its quality was collected, to display a graphical user interface comprising a left section, a center section, a right section, and a marker having a position within the left section, the center section, and/or the right section corresponding to a current orientation of the ultrasound device relative to the subject. The graphical user interface may be configured to operate as a bubble level.

In some embodiments, the processor-executable instructions, when executed by the at least one processor, cause the processing device, when configuring the ultrasound device to collect the multiple ultrasound images at the multiple elevational steering angles, to configure the ultrasound device to collect between or equal to approximately 4-50 ultrasound images.

According to an aspect of the present disclosure, an apparatus is provided, comprising a processing device in operative communication with an ultrasound device, the processing configured to instruct a user to collect multiple ultrasound images at multiple orientations relative to a subject select an ultrasound image of the multiple ultrasound images based on its quality; and configure the ultrasound device to continue to collect ultrasound images at an elevational steering angle corresponding to the orientation relative to the subject at which the ultrasound image selected based on its quality was collected.

In some embodiments, the processing device is configured, when instructing the user to collect the multiple ultrasound images at the multiple orientations relative to the subject, to instruct the user to fan the ultrasound device on the subject. The processing device is configured, when instructing the user to fan the ultrasound device on the subject, to instruct the user to move the ultrasound device in a short axis of an ultrasound transducer array of the ultrasound device approximately about a fixed point on the subject while changing an angle of insonation relative to the subject away from 90 degrees.

In some embodiments, the processing device is configured to configure the ultrasound device to use a constant elevational steering angle when collecting the multiple ultrasound images at the multiple orientations relative to the subject.

In some embodiments, the processing device is further configured to collect data regarding an orientation of the ultrasound device from one or more orientation sensors of the ultrasound device when each of the multiple ultrasound images is collected. The processing device is further configured to store each of the multiple ultrasound images along with an indication of data regarding an orientation of the ultrasound device used for collecting each of the multiple ultrasound images. The processing device is configured, when configuring the ultrasound device to continue to collect ultrasound images at the elevational steering angle corresponding to the orientation relative to the subject at which the ultrasound image selected based on its quality was collected, to determine the orientation at which the ultrasound image selected based on its quality was collected based on an indication stored along with this ultrasound image.

In some embodiments, the processing device is configured, when selecting the ultrasound image of the multiple ultrasound images based on its quality, to determine the quality of the selected ultrasound image by calculating a prediction of a collective opinion of a group of individuals regarding the clinical usability of the selected ultrasound image.

In some embodiments, the processing device is configured, when selecting the ultrasound image of the multiple ultrasound images based on its quality, to determine the quality of the selected ultrasound image by determining a presence or absence of landmarks in the selected ultrasound image.

In some embodiments, the processing device is configured, when selecting the ultrasound image of the multiple ultrasound images based on its quality, to determine the quality of the selected ultrasound image by determining a quality of one or more landmarks in the selected ultrasound image. The selected ultrasound image is an image of lungs, and the quality of the one or more landmarks is related to a height of a pleural line in the selected ultrasound image.

In some embodiments, the processing device is configured, when selecting the ultrasound image of the multiple ultrasound images based on its quality, to determine the quality of the selected ultrasound image by using a statistical model.

In some embodiments, the processing device is configured, when instructing the user to collect the multiple ultrasound images at the multiple orientations relative to the subject, to display a graphical user interface comprising an image of a subject and multiple images of an ultrasound device in different orientations relative to the image of the subject.

In some embodiments, the processing device is further configured to instruct the user to maintain the ultrasound device stationary while configuring the ultrasound device to continue to collect ultrasound images at the elevational steering angle corresponding to the orientation relative to the subject at which the ultrasound image selected based on its quality was collected.

According to an aspect of the present disclosure, a method is provided, comprising instructing, with a processing device in operative communication with an ultrasound device, a user of the ultrasound device to collect multiple ultrasound images at multiple orientations relative to a subject; selecting, with the processing device, an ultrasound image of the multiple ultrasound images based on its quality; and configuring, with the processing device, the ultrasound device to continue to collect ultrasound images at an elevational steering angle corresponding to the orientation relative to the subject at which the ultrasound image selected based on its quality was collected.

In some embodiments, instructing the user to collect the multiple ultrasound images at the multiple orientations relative to the subject comprises instructing the user to fan the ultrasound device on the subject. Instructing the user to fan the ultrasound device on the subject comprises instructing the user to move the ultrasound device in a short axis of an ultrasound transducer array of the ultrasound device approximately about a fixed point on the subject while changing an angle of insonation relative to the subject away from 90 degrees.

In some embodiments, configuring, with the processing device, the ultrasound device to use a constant elevational steering angle when collecting the multiple ultrasound images at the multiple orientations relative to the subject.

In some embodiments, collecting data regarding an orientation of the ultrasound device from one or more orientation sensors of the ultrasound device when each of the multiple ultrasound images is collected. Storing, with the processing device, each of the multiple ultrasound images along with an indication of data regarding an orientation of the ultrasound device used for collecting each of the multiple ultrasound images. When configuring the ultrasound device to continue to collect ultrasound images at the elevational steering angle corresponding to the orientation relative to the subject at which the ultrasound image selected based on its quality was collected, determining the orientation at which the ultrasound image selected based on its quality was collected based on an indication stored along with this ultrasound image.

In some embodiments, when selecting the ultrasound image of the multiple ultrasound images based on its quality, determining the quality of the selected ultrasound image by calculating a prediction of a collective opinion of a group of individuals regarding the clinical usability of the selected ultrasound image.

In some embodiments, when selecting the ultrasound image of the multiple ultrasound images based on its quality, determining the quality of the selected ultrasound image by determining a presence or absence of landmarks in the selected ultrasound image.

In some embodiments, when selecting the ultrasound image of the multiple ultrasound images based on its quality, determining the quality of the selected ultrasound image by determining a quality of one or more landmarks in the selected ultrasound image. The selected ultrasound image may be an image of lungs, and the quality of the one or more landmarks is related to a height of a pleural line in the selected ultrasound image.

In some embodiments, when selecting the ultrasound image of the multiple ultrasound images based on its quality, determining the quality of the selected ultrasound image by using a statistical model.

In some embodiments, when instructing the user to collect the multiple ultrasound images at the multiple orientations relative to the subject, displaying a graphical user interface comprising an image of a subject and multiple images of an ultrasound device in different orientations relative to the image of the subject.

In some embodiments, instructing the user to maintain the ultrasound device stationary while configuring the ultrasound device to continue to collect ultrasound images at the elevational steering angle corresponding to the orientation relative to the subject at which the ultrasound image selected based on its quality was collected.

According to an aspect of the present disclosure, at least one non-transitory computer-readable storage medium storing processor-executable instructions is provided that, when executed by at least one processor on a processing device in operative communication with an ultrasound device, cause the processing device to instruct a user to collect multiple ultrasound images at multiple orientations relative to a subject; select an ultrasound image of the multiple ultrasound images based on its quality; and configure the ultrasound device to continue to collect ultrasound images at an elevational steering angle corresponding to the orientation relative to the subject at which the ultrasound image selected based on its quality was collected.

In some embodiments, the processor-executable instructions, when executed by the at least one processor, cause the processing device, when instructing the user to collect the multiple ultrasound images at the multiple orientations relative to the subject, to instruct the user to fan the ultrasound device on the subject. The processor-executable instructions, when executed by the at least one processor, cause the processing device, when instructing the user to fan the ultrasound device on the subject, to instruct the user to move the ultrasound device in a short axis of an ultrasound transducer array of the ultrasound device approximately about a fixed point on the subject while changing an angle of insonation relative to the subject away from 90 degrees.

In some embodiments, the processor-executable instructions, when executed by the at least one processor, cause the processing device to configure the ultrasound device to use a constant elevational steering angle when collecting the multiple ultrasound images at the multiple orientations relative to the subject.

In some embodiments, the processor-executable instructions, when executed by the at least one processor, cause the processing device to collect data regarding an orientation of the ultrasound device from one or more orientation sensors of the ultrasound device when each of the multiple ultrasound images is collected. The processor-executable instructions, when executed by the at least one processor, cause the processing device to store each of the multiple ultrasound images along with an indication of data regarding an orientation of the ultrasound device used for collecting each of the multiple ultrasound images. The processor-executable instructions, when executed by the at least one processor, cause the processing device, when configuring the ultrasound device to continue to collect ultrasound images at the elevational steering angle corresponding to the orientation relative to the subject at which the ultrasound image selected based on its quality was collected, to determine the orientation at which the ultrasound image selected based on its quality was collected based on an indication stored along with this ultrasound image.

In some embodiments, the processor-executable instructions, when executed by the at least one processor, cause the processing device, when selecting the ultrasound image of the multiple ultrasound images based on its quality, to determine the quality of the selected ultrasound image by calculating a prediction of a collective opinion of a group of individuals regarding the clinical usability of the selected ultrasound image.

In some embodiments, the processing device is configured, when selecting the ultrasound image of the multiple ultrasound images based on its quality, to determine the quality of the selected ultrasound image by determining a presence or absence of landmarks in the selected ultrasound image.

In some embodiments, the processor-executable instructions, when executed by the at least one processor, cause the processing device, when selecting the ultrasound image of the multiple ultrasound images based on its quality, to determine the quality of the selected ultrasound image by determining a quality of one or more landmarks in the selected ultrasound image. The selected ultrasound image may be an image of lungs, and the quality of the one or more landmarks is related to a height of a pleural line in the selected ultrasound image.

In some embodiments, the processor-executable instructions, when executed by the at least one processor, cause the processing device, when selecting the ultrasound image of the multiple ultrasound images based on its quality, to determine the quality of the selected ultrasound image by using a statistical model.

In some embodiments, the processor-executable instructions, when executed by the at least one processor, cause the processing device, when instructing the user to collect the multiple ultrasound images at the multiple orientations relative to the subject, to display a graphical user interface comprising an image of a subject and multiple images of an ultrasound device in different orientations relative to the image of the subject.

In some embodiments, the processor-executable instructions, when executed by the at least one processor, cause the processing device to instruct the user to maintain the ultrasound device stationary while configuring the ultrasound device to continue to collect ultrasound images at the elevational steering angle corresponding to the orientation relative to the subject at which the ultrasound image selected based on its quality was collected.

Various aspects of the present disclosure may be used alone, in combination, or in a variety of arrangements not explicit in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Various inventive concepts may be embodied as one or more processes, of which an example has been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
   a processing device in operative communication with an ultrasound device, the processing device configured to:
   configure the ultrasound device to collect multiple ultrasound images from a subject at multiple elevational steering angles using beamforming while the ultrasound device is maintained stationary, the multiple ultrasound images including between approximately 4-50 ultrasound images;
   select an ultrasound image of the multiple ultrasound images based on its quality using a statistical model, wherein selecting comprises one or more of:
      determining the quality of the selected ultrasound image by calculating a prediction of a collective opinion of a group of individuals regarding the clinical usability of the selected ultrasound image;
      determining the quality of the selected ultrasound image by determining a presence or absence of one or more landmarks in the selected ultrasound image; or
      determining the quality of the selected ultrasound image by determining a quality of the one or more landmarks in the selected ultrasound image; and
   (a) instruct a user to continue to collect ultrasound images by moving the ultrasound device to an orientation relative to the subject corresponding to an elevational steering angle at which the ultrasound image selected based on its quality was collected by instructing the user to fan the ultrasound device to said orientation;
      configure the ultrasound device to collect multiple second ultrasound images from the subject at multiple second elevational steering angles while the ultrasound device is maintained stationary at said orientation;
      select a second ultrasound image of the multiple second ultrasound images based on its quality; and
      configure the ultrasound device to continue to collect ultrasound images at an elevational steering angle corresponding to the orientation relative to the subject at which the second ultrasound image selected based on its quality was collected;
   or (b) configure the ultrasound device to continue to collect ultrasound images at an elevational steering angle corresponding to the orientation relative to the subject at which the ultrasound image selected based on its quality was collected;
   wherein the processing device is a smartphone, tablet, or laptop.

2. The apparatus of claim 1, wherein selecting the ultrasound image of the multiple ultrasound images based on its quality using the statistical model comprises using a multi-layer neural network.

3. The apparatus of claim 1, wherein the selected ultrasound image is an image of lungs.

4. The apparatus of claim 3, wherein the collective opinion of a group of individuals regarding the clinical usability of the selected ultrasound image is a collective opinion of the usefulness of the selected ultrasound image for evaluating B-lines in the selected ultrasound image.

5. The apparatus of claim 3, wherein the one or more landmarks are anatomical markers of the lungs.

6. The apparatus of claim 1, wherein the processing device is configured, when selecting the ultrasound image of the multiple ultrasound images based on its quality, to determine the quality of the selected ultrasound image through a combination of two or more of calculating a prediction of a collective opinion of a group of individuals regarding the clinical usability of the selected ultrasound image, determining a presence of an anatomical feature in the selected image, or determining a quality of the one or more landmarks in the selected ultrasound image.

7. The apparatus of claim 1, wherein the processing device is configured, when instructing the user to continue to collect the ultrasound images by moving the ultrasound device to the orientation relative to the subject corresponding to the elevational steering angle at which the ultrasound image selected based on its quality was collected, to display a graphical user interface comprising a left section, a center section, a right section, and a marker having a position within the left section, the center section, and/or the right section corresponding to a current orientation of the ultrasound device relative to the subject.

8. A method, comprising:
   configuring, with a processing device in operative communication with an ultrasound device, the ultrasound device to collect multiple ultrasound images from a subject at multiple elevational steering angles;
   selecting, with the processing device, an ultrasound image of the multiple ultrasound images based on its quality; and
   (a) instructing, with the processing device, a user to continue to collect ultrasound images by moving the ultrasound device to an orientation relative to the subject corresponding to an elevational steering angle at which the ultrasound image selected based on its quality was collected by instructing the user to fan the ultrasound device to said orientation;
   configuring the ultrasound device to collect multiple second ultrasound images from a subject at multiple second elevational steering angles while the ultrasound device is maintained stationary at said orientation;
   selecting a second ultrasound image of the multiple second ultrasound images based on its quality; and
   configuring the ultrasound device to continue to collect ultrasound images at an elevational steering angle corresponding to the orientation relative to the subject at which the second ultrasound image selected based on its quality was collected;
   or (b) configure the ultrasound device to continue to collect ultrasound images at an elevational steering angle corresponding to the orientation relative to the subject at which the ultrasound image selected based on its quality was collected.

9. The method of claim 8, wherein configuring the ultrasound device to collect the multiple ultrasound images from the subject at the multiple elevational steering angles comprises configuring the ultrasound device to use beamforming.

10. The method of claim 8, wherein selecting the ultrasound image of the multiple ultrasound images based on its quality comprises determining the quality of the selected ultrasound image by calculating a prediction of a collective opinion of a group of individuals regarding the clinical usability of the selected ultrasound image.

11. The method of claim 8, wherein selecting the ultrasound image of the multiple ultrasound images based on its quality comprises determining the quality of the selected ultrasound image by determining a presence or absence of landmarks in the selected ultrasound image.

12. The method of claim 8, wherein selecting the ultrasound image of the multiple ultrasound images based on its quality comprises determining the quality of the selected ultrasound image by determining a quality of one or more landmarks in the selected ultrasound image.

13. The method of claim 8, wherein selecting the ultrasound image of the multiple ultrasound images based on its quality comprises determining the quality of the selected ultrasound image through a combination of two or more of calculating a prediction of a collective opinion of a group of individuals regarding the clinical usability of the selected ultrasound image, determining a presence of an anatomical feature in the selected image, or determining a quality of one or more landmarks in the selected ultrasound image.

14. The method of claim 8, further comprising, when instructing the user to continue to collect the ultrasound images by moving the ultrasound device to the orientation relative to the subject corresponding to the elevational steering angle at which the ultrasound image selected based on its quality was collected, displaying a graphical user interface comprising a left section, a center section, a right section, and a marker having a position within the left section, the center section, and/or the right section corresponding to a current orientation of the ultrasound device relative to the subject.

* * * * *